US010059703B2

(12) United States Patent
Lorsbach et al.

(10) Patent No.: US 10,059,703 B2
(45) Date of Patent: *Aug. 28, 2018

(54) 3-ALKYL-5-FLUORO-4-SUBSTITUTED-IMINO-3,4-DIHYDROPYRIMIDIN-2(1H)-ONE DERIVATIVES AS FUNGICIDES

(71) Applicant: Adama Makhteshim Ltd., Beer Sheva (IL)

(72) Inventors: Beth Lorsbach, Indianapolis, IN (US); Ronald Ross, Jr., Zionsville, IN (US); W. John Owen, Carmel, IN (US); Jeffery D. Webster, New Palestine, IN (US); Lindsay Stelzer, Indianapolis, IN (US); Chenglin Yao, Westfield, IN (US); Paul R. LePlae, Jr., Brownsburg, IN (US); Chris V. Galliford, Lafayette, IN (US)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/589,733

(22) Filed: May 8, 2017

(65) Prior Publication Data

US 2017/0240540 A1  Aug. 24, 2017

Related U.S. Application Data

(63) Continuation of application No. 14/655,570, filed as application No. PCT/US2013/077542 on Dec. 23, 2013.

(60) Provisional application No. 61/747,683, filed on Dec. 31, 2012.

(51) Int. Cl.
| | |
|---|---|
| *C07D 417/12* | (2006.01) |
| *A01N 43/54* | (2006.01) |
| *A01N 47/18* | (2006.01) |
| *A01N 43/78* | (2006.01) |
| *A01N 47/22* | (2006.01) |
| *C07D 409/12* | (2006.01) |
| *C07D 413/12* | (2006.01) |
| *C07D 239/47* | (2006.01) |
| *C07D 403/12* | (2006.01) |
| *C07B 59/00* | (2006.01) |
| *A01N 43/56* | (2006.01) |
| *A01N 43/80* | (2006.01) |

(52) U.S. Cl.
CPC .......... *C07D 417/12* (2013.01); *A01N 43/54* (2013.01); *A01N 43/56* (2013.01); *A01N 43/78* (2013.01); *A01N 43/80* (2013.01); *A01N 47/18* (2013.01); *A01N 47/22* (2013.01); *C07B 59/002* (2013.01); *C07D 239/47* (2013.01); *C07D 403/12* (2013.01); *C07D 409/12* (2013.01); *C07D 413/12* (2013.01); *C07B 2200/05* (2013.01)

(58) Field of Classification Search
CPC .. C07D 417/12; C07D 239/47; C07D 409/12; C07D 403/12; C07D 413/12; A01N 43/54; A01N 43/56; A01N 43/78; A01N 43/80; A01N 47/22; A01N 47/18; C07B 2200/05; C07B 59/002
See application file for complete search history.

(56) References Cited

U.S. PATENT DOCUMENTS

| | | | |
|---|---|---|---|
| 3,309,359 | A | 3/1967 | Duschinsky et al. |
| 3,368,938 | A | 2/1968 | Berger et al. |
| 3,635,977 | A | 1/1972 | Lutz et al. |
| 3,868,373 | A | 2/1975 | Hoffer |
| 4,009,272 | A | 2/1977 | Konig et al. |
| 4,845,081 | A | 7/1989 | Sloan |
| 4,996,208 | A | 2/1991 | Lindner et al. |
| 5,962,489 | A | 10/1999 | Mueller et al. |
| 6,066,638 | A | 5/2000 | Bereznak et al. |
| 6,617,330 | B2 | 9/2003 | Walter |
| 7,914,799 | B2 | 3/2011 | Jira et al. |
| 8,263,603 | B2 | 9/2012 | Boebel et al. |
| 8,318,758 | B2 | 11/2012 | Boebel et al. |
| 8,470,839 | B2 | 6/2013 | Boebel et al. |
| 8,552,020 | B2 | 10/2013 | Pobanz et al. |
| 8,658,660 | B2 | 2/2014 | Boebel et al. |
| 8,916,579 | B2 | 12/2014 | Boebel et al. |
| 9,000,002 | B2 | 4/2015 | Pobanz et al. |
| 9,006,259 | B2 | 4/2015 | Webster et al. |
| 9,174,970 | B2 | 11/2015 | Benko et al. |
| 9,204,653 | B2 | 12/2015 | Boebel et al. |

(Continued)

FOREIGN PATENT DOCUMENTS

| | | |
|---|---|---|
| AU | 2008/249329 | 11/2008 |
| CN | 102548980 A | 7/2012 |

(Continued)

OTHER PUBLICATIONS

PCT International Search Report dated Sep. 21, 2010 in connection with PCT International Application No. PCT/US2010/044579 (WO 2011/017540), filed Aug. 5, 2010.

(Continued)

*Primary Examiner* — Alexander R Pagano
*Assistant Examiner* — Ebenezer O Sackey
(74) *Attorney, Agent, or Firm* — Gary J. Gershik; Cooper & Dunham LLP

(57) ABSTRACT

This present disclosure is related to the field of 3-alkyl-5-fluoro-4-substituted-imino-3,4-5 dihydropyrimidin-2(1H)-ones and their derivatives and to the use of these compounds as fungicides. Also provided are methods of controlling a fungal disease such as *Septoria tritici*, comprising administering an effective amount of the fungicide compound to at lease one surface associated with the plant, seed or soil.

20 Claims, No Drawings

(56) References Cited

U.S. PATENT DOCUMENTS

| | | |
|---|---|---|
| 9,271,497 B2 | 3/2016 | Lorsbach et al. |
| 9,321,734 B2 | 4/2016 | Lorsbach et al. |
| 9,526,245 B2 | 12/2016 | Owen et al. |
| 9,532,570 B2 | 1/2017 | Owen et al. |
| 9,538,753 B2 | 1/2017 | Owen et al. |
| 9,622,474 B2 | 4/2017 | Lorsbach et al. |
| 9,642,368 B2 | 5/2017 | Lorsbach et al. |
| 9,840,475 B2 | 12/2017 | Lorsbach et al. |
| 9,840,476 B2 | 12/2017 | Choy et al. |
| 9,850,215 B2 | 12/2017 | Choy et al. |
| 9,862,686 B2 | 1/2018 | Boebel et al. |
| 2003/0039667 A1 | 2/2003 | Jira et al. |
| 2007/0027034 A1 | 2/2007 | Tank et al. |
| 2008/0004253 A1 | 1/2008 | Branstetter et al. |
| 2008/0182847 A1 | 7/2008 | Augeri et al. |
| 2008/0269238 A1 | 10/2008 | Sugihara et al. |
| 2008/0280917 A1 | 11/2008 | Albrecht et al. |
| 2009/0203647 A1 | 8/2009 | Benko et al. |
| 2010/0022538 A1 | 1/2010 | Boebel et al. |
| 2010/0029482 A1 | 2/2010 | Benko et al. |
| 2010/0029483 A1 | 2/2010 | Iskandar et al. |
| 2010/0284959 A1 | 11/2010 | Rayan et al. |
| 2011/0034490 A1 | 2/2011 | Boebel et al. |
| 2011/0034491 A1 | 2/2011 | Boebel et al. |
| 2011/0034492 A1 | 2/2011 | Boebel et al. |
| 2011/0034493 A1 | 2/2011 | Boebel et al. |
| 2011/0053891 A1 | 3/2011 | Boebel et al. |
| 2011/0082162 A1 | 4/2011 | Lorsbach et al. |
| 2011/0263627 A1 | 10/2011 | Boebel et al. |
| 2012/0208700 A1 | 8/2012 | Hopkins et al. |
| 2013/0045984 A1 | 2/2013 | Boebel et al. |
| 2014/0011824 A1 | 1/2014 | Pobanz et al. |
| 2014/0024616 A1 | 1/2014 | Boebel et al. |
| 2015/0111851 A1 | 4/2015 | Boebel et al. |
| 2015/0181874 A1 | 7/2015 | Owen et al. |
| 2015/0181875 A1 | 7/2015 | Owen et al. |
| 2015/0181883 A1 | 7/2015 | Owen et al. |
| 2015/0183749 A1 | 7/2015 | Choy et al. |
| 2015/0183750 A1 | 7/2015 | Choy et al. |
| 2015/0191436 A1 | 7/2015 | Webster et al. |
| 2015/0342188 A1 | 12/2015 | Lorsbach et al. |
| 2015/0353506 A1 | 12/2015 | Lorsbach et al. |
| 2015/0359225 A1 | 12/2015 | Lorsbach et al. |
| 2016/0192653 A1 | 7/2016 | Lorsbach et al. |
| 2016/0198711 A1 | 7/2016 | Lorsbach et al. |
| 2016/0280662 A1 | 9/2016 | Choy et al. |
| 2016/0280663 A1 | 9/2016 | Choy et al. |
| 2017/0008855 A1 | 1/2017 | Boebel et al. |
| 2017/0086458 A1 | 3/2017 | Owen et al. |
| 2017/0086459 A1 | 3/2017 | Owen et al. |
| 2017/0086460 A1 | 3/2017 | Owen et al. |
| 2017/0204069 A1 | 7/2017 | Lorsbach et al. |
| 2018/0000082 A1 | 1/2018 | Klittich et al. |

FOREIGN PATENT DOCUMENTS

| | | |
|---|---|---|
| CN | 102574831 A | 7/2012 |
| EP | 0102908 | 3/1984 |
| EP | 0139613 | 5/1985 |
| EP | 0332579 | 9/1989 |
| EP | 0877022 | 4/2003 |
| EP | 1798225 | 6/2007 |
| EP | 1798255 | 6/2007 |
| EP | 1952689 | 8/2008 |
| GB | 989455 | 4/1965 |
| GB | 1461184 | 1/1977 |
| JP | 60123486 | 7/1985 |
| JP | 6001793 | 1/1994 |
| JP | 2002-530409 | 9/2002 |
| JP | 2012-502905 | 2/2012 |
| JP | 2013-501728 | 1/2013 |
| JP | 5759991 | 8/2015 |
| WO | WO 1997/016456 A1 | 5/1997 |
| WO | WO 97/33890 A1 | 9/1997 |
| WO | WO 02/30922 A2 | 4/2002 |
| WO | WO 2004/037159 A2 | 5/2004 |
| WO | WO 2006/030606 A1 | 3/2006 |
| WO | WO 2008/083465 A1 | 7/2008 |
| WO | WO 2008/139394 A1 | 11/2008 |
| WO | WO 2009/094442 A2 | 7/2009 |
| WO | WO 2010/047866 A2 | 4/2010 |
| WO | WO 2010/085377 A2 | 7/2010 |
| WO | WO 2011/017538 A1 | 2/2011 |
| WO | WO 2011/017540 A1 | 2/2011 |
| WO | WO 2011/017544 A1 | 2/2011 |
| WO | WO 2011/017545 A1 | 2/2011 |
| WO | WO 2011/017547 A1 | 2/2011 |
| WO | WO 2011/137002 A1 | 11/2011 |
| WO | WO 2012/108873 A1 | 8/2012 |
| WO | WO 2013/025795 A1 | 2/2013 |
| WO | WO 2013/113781 A1 | 8/2013 |
| WO | WO 2014/105821 A1 | 7/2014 |
| WO | WO 2014/105841 A1 | 7/2014 |
| WO | WO 2014/105844 A1 | 7/2014 |
| WO | WO 2014/105845 A1 | 7/2014 |
| WO | WO 2015/103142 A1 | 7/2015 |
| WO | WO 2015/103144 A1 | 7/2015 |
| WO | WO 2015/103259 A1 | 7/2015 |
| WO | WO 2015/103261 A1 | 7/2015 |
| WO | WO 2015/103262 A1 | 7/2015 |
| WO | WO 2016/106138 A1 | 6/2016 |

OTHER PUBLICATIONS

Written Opinion of the International Searching Authority dated Sep. 21, 2010 in connection with PCT International Application No. PCT/US2010/044579 (WO 2011/017540), filed Aug. 5, 2010.

International Preliminary Report on Patentability dated Feb. 7, 2012 in connection with PCT International Application No. PCT/US2010/044579 (WO 2011/017540), filed Aug. 5, 2010.

PCT International Search Report dated Sep. 21, 2010 in connection with PCT International Application No. PCT/US2010/044592 (WO 2011/017547), filed Aug. 5, 2010.

Written Opinion of the International Searching Authority dated Sep. 21, 2010 in connection with PCT International Application No. PCT/US2010/044592 (WO 2011/017547), filed Aug. 5, 2010.

International Preliminary Report on Patentability dated Feb. 7, 2012 in connection with PCT International Application No. PCT/US2010/044592 (WO 2011/017547), filed Aug. 5, 2010.

PCT International Search Report dated Sep. 23, 2010 in connection with PCT International Application No. PCT/US2010/044576 (WO 2011/017538), filed Aug. 5, 2010.

Written Opinion of the International Searching Authority dated Sep. 23, 2010 in connection with PCT International Application No. PCT/US2010/044576 (WO 2011/017538), filed Aug. 5, 2010.

International Preliminary Report on Patentability dated Feb. 7, 2012 in connection with PCT International Application No. PCT/US2010/044576 (WO 2011/017538), filed Aug. 5, 2010.

PCT International Search Report dated Sep. 23, 2010 in connection with PCT International Application No. PCT/US2010/044585 (WO 2011/017544), filed Aug. 5, 2010.

Written Opinion of the International Searching Authority dated Sep. 23, 2010 in connection with PCT International Application No. PCT/US2010/044585 (WO 2011/017544), filed Aug. 5, 2010.

International Preliminary Report on Patentability dated Feb. 7, 2012 in connection with PCT International Application No. PCT/US2010/044585 (WO 2011/017544), filed Aug. 5, 2010.

PCT International Search Report dated Oct. 1, 2010 in connection with PCT International Application No. PCT/US2010/044588 (WO 2011/017545), filed Aug. 5, 2010.

Written Opinion of the International Searching Authority dated Oct. 1, 2010 in connection with PCT International Application No. PCT/US2010/044588 (WO 2011/017545), filed Aug. 5, 2010.

International Preliminary Report on Patentability dated Feb. 7, 2012 in connection with PCT International Application No. PCT/US2010/044588 (WO 2011/017545), filed Aug. 5, 2010.

PCT International Search Report dated Jul. 5, 2011 in connection with PCT International Application No. PCT/US2011/033203 (WO 2011/137002), filed Apr. 20, 2011.

(56) References Cited

OTHER PUBLICATIONS

Written Opinion of the International Searching Authority dated Jul. 5, 2011 in connection with PCT International Application No. PCT/US2011/033203 (WO 2011/137002), filed Apr. 20, 2011.
International Preliminary Report on Patentability dated Oct. 30, 2012 in connection with PCT International Application No. PCT/US2011/033203 (WO 2011/137002), filed Apr. 20, 2011.
PCT International Search Report dated Oct. 15, 2012 in connection with PCT International Application No. PCT/US2012/050930 (WO 2013/025795), filed Aug. 15, 2012.
Written Opinion of the International Searching Authority dated Oct. 15, 2012 in connection with PCT International Application No. PCT/US2012/050930 (WO 2013/025795), filed Aug. 15, 2012.
International Preliminary Report on Patentability dated Feb. 18, 2014 in connection with PCT International Application No. PCT/US2012/050930 (WO 2013/025795), filed Aug. 15, 2012.
PCT International Search Report dated Apr. 22, 2014 in connection with PCT International Application No. PCT/US2013/077542 (WO 2014/105845), filed Dec. 23, 2013.
Written Opinion of the International Searching Authority dated Apr. 22, 2014 in connection with PCT International Application No. PCT/US2013/077542 (WO 2014/105845), filed Dec. 23, 2013.
International Preliminary Report on Patentability dated Jun. 30, 2015 in connection with PCT International Application No. PCT/US2013/077542 (WO 2014/105895), filed Dec. 23, 2013.
PCT International Search Report dated Apr. 24, 2014 in connection with PCT International Application No. PCT/US2013/077540 (WO 2014/105844), filed Dec. 23, 2013.
Written Opinion of the International Searching Authority dated Apr. 24, 2014 in connection with PCT International Application No. PCT/US2013/077540 (WO 2014/105844), filed Dec. 23, 2013.
International Preliminary Report on Patentability dated Jun. 30, 2015 in connection with PCT International Application No. PCT/US2013/077540 (WO 2014/105894), filed Dec. 23, 2013.
PCT International Search Report dated Apr. 28, 2014 in connection with PCT International Application No. PCT/US2013/077533 (WO 2014/105841), filed Dec. 23, 2013.
Written Opinion of the International Searching Authority dated Apr. 28, 2014 in connection with PCT International Application No. PCT/US2013/077533 (WO 2014/105841), filed Dec. 23, 2013.
International Preliminary Report on Patentability dated Jun. 30, 2015 in connection with PCT International Application No. PCT/US2013/077533 (WO 2014/105841), filed Dec. 23, 2013.
PCT International Search Report dated Apr. 28, 2014 in connection with PCT International Application No. PCT/US2013/077478 (WO 2014/105821), filed Dec. 23, 2013.
Written Opinion of the International Searching Authority dated Apr. 28, 2014 in connection with PCT International Application No. PCT/US2013/077478 (WO 2014/105821), filed Dec. 23, 2013.
International Preliminary Report on Patentability dated Jun. 30, 2015 in connection with PCT International Application No. PCT/US2013/077478 (WO 2014/105821), filed Dec. 23, 2013.
PCT International Search Report dated Apr. 8, 2015 in connection with PCT International Application No. PCT/US2014/072566 (WO 2015/103142), filed Dec. 29, 2014.
International Preliminary Report on Patentability dated Jul. 5, 2016 in connection with PCT International Application No. PCT/US2014/072566 (WO 2015/103142), filed Dec. 29, 2014.
Written Opinion of the International Searching Authority dated Apr. 8, 2015 in connection with PCT International Application No. PCT/US2014/072566 (WO 2015/103142), filed Dec. 29, 2014.
PCT International Search Report dated Apr. 2, 2015 in connection with PCT International Application No. PCT/US2014/072569 (WO 2015/103144), filed Dec. 29, 2014.
International Preliminary Report on Patentability dated Jul. 5, 2016 in connection with PCT International Application No. PCT/US2014/072569 (WO 2015/103144), filed Dec. 29, 2014.
Written Opinion of the International Searching Authority dated Apr. 2, 2015 in connection with PCT International Application No. PCT/US2014/072569 (WO 2015/103144), filed Dec. 29, 2014.

PCT International Search Report dated Apr. 28, 2015 in connection with PCT International Application No. PCT/US2014/072745 (WO 2015/103259), filed Dec. 30, 2014.
International Preliminary Report on Patentability dated Jul. 5, 2016 in connection with PCT International Application No. PCT/US2014/072745 (WO 2015/103259), filed Dec. 30, 2014.
Written Opinion of the International Searching Authority dated Apr. 28, 2015 in connection with PCT International Application No. PCT/US2014/072745 (WO 2015/103259), filed Dec. 30, 2014.
PCT International Search Report dated Apr. 29, 2015 in connection with PCT International Application No. PCT/US2014/072747 (WO 2015/103261), filed Dec. 30, 2014.
International Preliminary Report on Patentability dated Jul. 5, 2016 in connection with PCT International Application No. PCT/US2014/072747 (WO 2015/103261), filed Dec. 30, 2014.
Written Opinion of the International Searching Authority dated Apr. 29, 2015 in connection with PCT International Application No. PCT/US2014/072747 (WO 2015/103261), filed Dec. 30, 2014.
PCT International Search Report dated May 21, 2015 in connection with PCT International Application No. PCT/US2014/072748 (WO 2015/103262), filed Dec. 30, 2014.
International Preliminary Report on Patentability dated Jul. 5, 2016 in connection with PCT International Application No. PCT/US2014/072748 (WO 2015/103262), filed Dec. 30, 2014.
Written Opinion of the International Searching Authority dated May 21, 2015 in connection with PCT International Application No. PCT/US2014/072748 (WO 2015/103262), filed Dec. 30, 2014.
PCT International Search Report dated Feb. 25, 2016 in connection with PCT International Application No. PCT/US2015/066756 (WO 2016/106138), filed Dec. 18, 2015.
International Preliminary Report on Patentability dated Jun. 27, 2017 in connection with PCT International Application No. PCT/US2015/066756 (WO 2016/106138), filed Dec. 18, 2015.
Written Opinion of the International Searching Authority dated Feb. 25, 2016 in connection with PCT International Application No. PCT /US2015/066756 (WO 2016/106138), filed Dec. 18, 2015.
PCT International Search Report dated Sep. 30, 2009 in connection with PCT International Application No. PCT/US/2009/031683 (WO 2009/094442), filed Jan. 22, 2009.
PCT International Search Report dated Mar. 14, 2011 in connection with PCT International Application No. PCT/US/2011/020351 (WO 2011/085084), filed Jan. 6, 2011.
PCT International Search Report dated Oct. 1, 2010 in connection with PCT International Application No. PCT/US/2010/044588 (WO 2011/017545), filed Aug. 5, 2010.
PCT International Search Report dated Oct. 9, 2012 in connection with PCT International Application No. PCT/US/2012/050931 (WO 2013/025796), filed Aug. 15, 2012.
PCT International Search Report dated Apr. 22, 2011 in connection with PCT International Application No. PCT/US/2010/060792 (WO 2011/084611), filed Dec. 16, 2010.
May 5, 2016 Non-Final Office Action issued by the U.S. Patent and Trademark Office in connection with U.S. Appl. No. 14/655,570.
Oct. 5, 2016 Response to May 5, 2016 Non-Final Office Action issued by the U.S. Patent and Trademark Office in connection with U.S. Appl. No. 14/655,570.
Sep. 26, 2016 Patent Examination Report No. 1 issued by Australian Patent Office in connection with Australian Patent Application No. 2013370494.
Jun. 27, 2017 Response to Sep. 26, 2016 Patent Examination Report No. 1 issued by Australian Patent Office in connection with Australian Patent Application No. 2013370494.
Aug. 3, 2016 European Supplemental Search Report issued by the European Patent Office in connection with European Patent Application No. 13869177.9.
Aug. 22, 2016 Communication pursuant to Rules 70(2) and 70a(2) issued by the European Patent Office in connection with European Patent Application No. 13869177.9.
Feb. 27, 2017 Response dated Aug. 22, 2016 Communication pursuant to Rules 70(2) and 70a(2) issued by the European Patent Office in connection with European Patent Application No. 13869177.9.

(56) References Cited

OTHER PUBLICATIONS

Aug. 10, 2016 Office Action issued by the Chinese Patent Office in connection with Chinese Patent Application No. 201380073784.4.
Dec. 26, 2016 Response dated Aug. 10, 2016 Office Action issued by the Chinese Patent Office in connection with Chinese Patent Application No. 201380073784.4.
Apr. 27, 2017 Second Office Action issued by the Chinese Patent Office in connection with Chinese Patent Application No. 2013 8 0073784.4.
Jul. 12, 2017 Response dated Apr. 27, 2017 Second Office Action issued by the Chinese Patent Office in connection with Chinese Patent Application No. 201380073784.4.
Oct. 15, 2015 Response dated Aug. 18, 2015 Office Action issued by the Colombian Patent Office in connection with Colombian Patent Application No. 15177787.
Sep. 12, 2016 Office Action issued by the Colombian Patent Office in connection with Colombian Patent Application No. 15177787.
Jan. 25, 2017 Response dated Sep. 12, 2016 Office Action issued by the Colombian Patent Office in connection with Colombian Patent Application No. 15177787.
May 28, 2017 Response dated Oct. 27, 2016 Office Action issued by the Israeli Patent Office in connection with Israeli Patent Application No. 239597.
Jan. 19, 2016 Report on State of the Art issued by the Panama Patent Office in connection with Panama Patent Application No. 90742-01.
Jan. 12, 2017 Response dated Jan. 19, 2016 Report on State of the Art issued by the Panama Patent Office in connection with Panama Patent Application No. 90742-01.
Bera et al. (2002) "Nucleosides with furanyl scaffolds." Tetrahedron, Elsevier Science Publishers. 58(24): 4865-4871.
Sera, et al. (2002) CAPLUS Abstract 137:279407.
Chiaccio et al. (2003) "Enantioselective Syntheses and Cytotoxicity of N,O-Nucleosides." J. of Medicinal Chemistry, American Chemical Society. 46(1): 3696-3702.
Duschinsky et al. (1966) "Nucleosides. XXXIII. N4-Acylated 5-Fluorocytosines and a Direct Synthesis of 5-Fluoro-2'-deoxycytidine" J. of Medicinal Chemistry. 9(4): 566-572.
Duschinsky et al. (1964) "Cytosine derivatives." CAPLUS Abstract 61:18527.
Gabriella et al. (1963) "Some 5-fluorosulfanilamidopyrimidines." Gazzette Chimica Italiana. 93(10): 1268-1278.
Jaworski et al. (1990) "Infrared spectra and tautomerism of 5-fluorocytosine, 5-bromocytosine and 5-iodocytosine Matrix isolation and theoretical ab initio studies." J. of Molecular Structure. 223: 63-92.
Koch et al. (1987) "N-Mannich base derivatives of 5-fluorocytosine: a prodrug approach to improve topical delivery." International Journal of Pharmaceutics. 35:243-252.
Kulikowski et al. (1978) "Methylation and tautomerism of 5-fluorocytosine nucleosides and their analogues." J. Nucleic Acids Research, Special Publication. 4(1) : S7-510.
Lewis et al. (2007) "Synthesis and in vitro anti-human cytomegalovirus (hcmv) activity of certain alkenyl substituted cytosines and 5-halocytosines." J. of Heterocyclic Chemistry. 32(5): 1513-1515.
Liang et al. (2007) "A facile synthesis and herbicidal activities of novel fluorine-containing thiazolo [4,5-d] pyrimidin-7 (6H)-ones." J. of Fluorine Chemistry, 128(7): 879-884.

Mao et al. (2004) "Synthesis of enantiomerically pure D-FDOC, an anti-HIV agent." Bioorganic & Medicinal Chemistry Letters, 14:4992-4994.
Ogilvie et al. (2007) "Synthesis of 5-Substituted-1-1[2-Hydroxy-1 (hyrdomethyl) ethoxy]methyl] cytisines." Nucleosides and Nucleotides. 2(2): 147-154 (Abstract Only).
Redha, et al. (2009) "Synthesis of New Dihydropyrimidine-2-(1H)-one Compounds" Al-Mustansiriya J. Sci. 20(3): 53-65.
Robins et al. (1972) "A direct synthesis of 5-fluorocytosine and its nucleosides using trifluromethyl hypofluorite." J. of the Chemical Society, Chemical Communications. 1(1): 18.
Waring (2009) "Defining optimum lipophilicity and molecular weight ranges for drug candidates—Molecular weight dependent lower logD limits based on permeability." Bioorganic & Medicinal Chemistry Letters, 19(10): 2844-2851.
Woese et al, (1990) "Towards a natural system of organisms: Proposal for the domains Archaea, Bacteria, and Eucarya." Proc. Acad. Sci., 87:4576-4579.
Ying Cai et al. (2004) "Alkaline protease from Bacillus subtilis Catalyzed Michael Addition of Pyrimidine Derivatives to a.p-Ethylenic Compounds in Organic Media." Synthesis, 2004 (5): 671-674.
Zhang et al. (1989) "Improved method for synthesis of 5-fluorocytosine (5-FC)." CAPLUS Abstract, 111:134074.
CAS RN 500886-59-9; STN entry date: Mar. 28, 2003, 4-Amino-N,N-diethyl-5-fluoro-2-oxo-1(2H)-pyrimidineacetamide.
CAS RN 958785-38-1; STN entry date: Dec. 19, 2007, 4-Amino-1-[[2-(chloromethyl) phenyl]methyl]-5-fluoro-2(1H)-pyrimidinon.
CAS RN 500881-49-2; STN entry date Mar. 28, 2003, 4-(Acetylamino)-N,N-diethyl-5-fluoro-2-oxo-1(2H)-pyrimidinaeecetamide.
CAS RN 392662-90-7; STN entry date: Feb. 15, 2002, 4-Amino-1-(2,4-dihydroxybutyl)-5-fluoro-2(1 H)-pyrimidinone.
CAS RN 313521-37-8; STN entry date: Jan. 11, 2001, 4-Amino-1-(2,3-dihydroxypropyl)-5-fluoro-2(1 H)-pyrimidinone.
Database Registry [Online] Chemical Abstracts Service, 2008, Database accession No. 1080650-20-9, 4-amino-5-fluoro-2-oxo-2(1H)-pyrimidineaceti ethyl ester.
Database Registry [Online] Chemical Abstracts Service, Columbus, 2009, Database accession No. 1135026-00-4, 4-amino-N,N-diethyl-5-fluoro-2-oxo-(1H)-pyrimidinacetamide hydrochloride).
CAS Registry File RN: 2711-88-8 and 2357-24-6, N-(5-fluoro-2,3-dihydro-2-oxo-4-pyrimidinyl)-4-methylbenzamide.
Database Registry [Online] Chemical Abstracts Service, entry date: May 1, 1962, 89829-72-1.
Nov. 2, 2017 Communication pursuant to Article 94(3) EPC issued by the European Patent Office in connection with European Patent Application No. 13869177.9.
Oct. 13, 2017 Third Office Action issued by the Chinese Patent Office in connection with Chinese Patent Application No. 201380073784.4 (including English language translation).
Dec. 28, 2017 Response dated Oct. 13, 2017 Third Office Action issued by the Chinese Patent Office in connection with Chinese Patent Application No. 201380073784.4.
Oct. 15, 2017 Response dated Jun. 14, 2017 Office Action issued by the Israeli Patent Office in connection with Israeli Patent Application No. 239597.
Oct. 31, 2017 Office Action issued by the Japanese Patent Office in connection with Japanese Patent Application No. 2015-550744 (including English language translation).
Ledochowski et al. (1967) Roczniki Chemii. 41:215-220.

3-ALKYL-5-FLUORO-4-SUBSTITUTED-IMINO-3,4-DIHYDROPYRIMIDIN-2(1H)-ONE DERIVATIVES AS FUNGICIDES

CROSS REFERENCE TO RELATED APPLICATIONS

This application is a continuation of U.S. Ser. No. 14/655,570, filed Jun. 25, 2015, which claims the benefit of U.S. Provisional Patent Application Ser. No. 61/747,683 filed Dec. 31, 2012, which is expressly incorporated by reference herein.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to 3-alkyl-5-fluoro-4-imino-3,4-dihydropyrimidin-2(1H)one compounds and their use as fungicides. The compounds of the present disclosure may offer protection against ascomycetes, basidiomycetes, deuteromycetes and oomycetes.

One embodiment of the present disclosure may include compounds of Formula I:

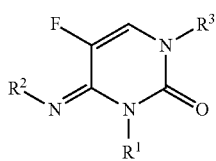

Formula I wherein $R^1$ is:
  $C_1$-$C_6$ alkyl optionally substituted with 1-3 $R^4$;
  —C(=O)$R^5$;
  —C(=O)O$R^5$;
  —CH$_2$OC(=O)$R^5$; or
  —(CHR$^8$)$_n$$R^7$;
$R^2$ is:
  $C_1$-$C_6$ alkyl optionally substituted with 1-3 $R^6$;
  —C(=O)$R^7$;
  —C(=O)O$R^7$; or
  —(CHR$^8$)$_n$$R^7$;
  wherein n is an integer from 1-3;
$R^3$ is —S(O)$_2$$R^9$;
$R^4$ is independently $C_1$-$C_6$ alkyl, $C_1$-$C_4$ alkoxy, $C_1$-$C_4$ haloalkoxy, $C_1$-$C_4$ alkylthio, haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, deuterium, or $C_3$-$C_6$ trialkylsilyl;
$R^5$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^{10}$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^{10}$, biphenyl or naphthyl optionally substituted with 1-3 $R^{10}$;
$R^6$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, deuterium, or $C_3$-$C_6$ trialkylsilyl;
$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^{10}$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^{10}$, biphenyl or naphthyl optionally substituted with 1-3 $R^{10}$;
$R^8$ is H, $C_1$-$C_6$ alkyl, or $C_1$-$C_6$ haloalkyl;
$R^9$ is $C_1$-$C_6$ alkyl, $C_1$-$C_6$ haloalkyl, amino, $C_1$-$C_6$ alkylamino, $C_2$-$C_6$ dialkylamino, a phenyl or benzyl wherein each of the phenyl or the benzyl may be optionally substituted with 1-3 $R^{10}$, or a 5- or 6-membered saturated or unsaturated ring containing 1-3 heteroatoms wherein each ring may be optionally substituted with 1-3 $R^{10}$, or with a 5-6 fused ring system, or with a 6-6 fused ring system each containing 1-3 heteroatoms wherein each ring may be optionally substituted with 1-3 $R^{10}$, biphenyl or naphthyl optionally substituted with 1-3 $R^{10}$; and
$R^{10}$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_6$ alkylamino, $C_2$-$C_6$ alkoxycarbonyl, $C_2$-$C_6$ alkylcarbonyl, $C_2$-$C_6$ alkylaminocarbonyl, $C_2$-$C_6$ dialkylamino, hydroxy, cyano, or nitro.

In a further embodiment, $R^4$ is independently $C_1$-$C_6$ alkyl, $C_1$-$C_4$ alkoxy, $C_1$-$C_4$ alkylthio, hydroxyl, or deuterium.

In still another embodiment, $R^5$ is $C_1$-$C_6$ alkyl, $C_1$-$C_6$ haloalkyl, phenyl or benzyl wherein each of the phenyl or the benzyl may be optionally substituted with 1-3 $R^{10}$.

In yet another embodiment, $R^6$ is independently halogen, $C_1$-$C_6$ alkyl, $C_1$-$C_4$ haloalkyl, $C_1$-$C_4$ alkoxy, $C_1$-$C_4$ alkylthio, or deuterium.

In another embodiment, $R^7$ is $C_1$-$C_6$ alkyl, $C_1$-$C_6$ haloalkyl, phenyl or benzyl wherein each of the phenyl or the benzyl may be optionally substituted with 1-3 $R^{10}$.

Still, in another embodiment, $R^{10}$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, cyano, or nitro.

In yet another embodiment, $R^9$ is phenyl optionally substituted with 1-3 $R^{10}$, or a 5- or 6-membered saturated or unsaturated ring containing 1-3 heteroatoms optionally substituted with 1-3 $R^{10}$. In a further embodiment, $R^{10}$ is independently halogen, $C_1$-$C_6$ alkyl, $C_1$-$C_4$ alkoxy, $C_1$-$C_4$ haloalkoxy.

In one embodiment, $R^1$ is $C_1$-$C_3$ alkyl. In another embodiment, $R^2$ is $C_1$-$C_3$ alkyl, —C(=O)$R^5$, or —C(=O)O$R^5$. In a further embodiment, $R^5$ is $C_1$-$C_3$ alkyl or phenyl. In another embodiment $R^1$ is $C_1$-$C_3$ alkyl.

In another embodiment, $R^9$ is selected from the group consisting of:

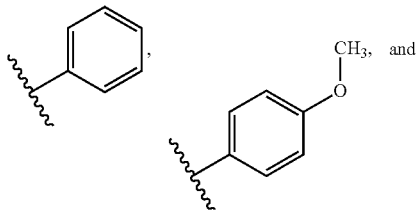

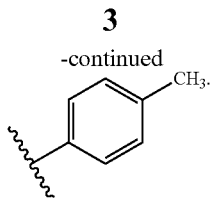

In a further embodiment, $R^2$ is $C_1$-$C_3$ alkyl, —C(=O)$R^5$, or —C(=O)O$R^5$. In another further embodiment, $R^5$ is $C_1$-$C_3$ alkyl or phenyl. In still another further embodiment, $R^1$ is $C_1$-$C_3$ alkyl.

Also proposed is a compound according to Formula I, wherein $R^1$ is: $C_1$-$C_6$ alkyl optionally substituted with 1-3 $R^4$;
—C(=O)$R^5$; or
—CH$_2$OC(=O)$R^5$;
$R^2$ is: $C_1$-$C_6$ alkyl optionally substituted with 1-3 $R^6$;
—C(=O)$R^7$; —C(=O)O$R^7$; or —(CH$R^8$)$_n$$R^7$;
$R^3$ is —S(O)$_2$$R^9$;
$R^4$ is hydroxyl, or deuterium;
$R^5$ is $C_1$-$C_6$ alkyl, or phenyl;
$R^6$ is deuterium;
$R^7$ is $C_1$-$C_6$ alkyl, or phenyl optionally substituted with 1-3 $R^{10}$;
$R^8$ is H; n is 1
$R^9$ is $C_1$-$C_6$ alkyl, or a phenyl optionally substituted with 1-3 $R^{10}$, or a 5- or 6-membered saturated or unsaturated ring containing 1-3 heteroatoms wherein each ring may be optionally substituted with 1-3 $R^{10}$; and
$R^{10}$ is independently halogen, $C_1$-$C_6$ alkyl, $C_1$-$C_4$ alkoxy, $C_1$-$C_4$ haloalkoxy, or cyano.

Also proposed is a composition for the control of a fungal pathogen, including; at least one compound of Formula I; and a phytologically acceptable carrier material, wherein said composition is effective for the control of at least one pathogenic fungus or pathogenic fungus like organism.

In a further embodiment, the pathogenic fungus or fungus like pathogen is *Septoria tritici*.

Also proposed is a method for treating a plant, comprising the steps of: applying a fungicidally effective amount of at least one of the compounds of Formula 1 to at least one surface, selected from the group of surfaces consisting of: at least one portion of a plant, an area adjacent to a plant, soil in contact with a plant, solid adjacent to a plant, a seed, and agricultural equipment.

In a further embodiment, the fungicidally effective amount Formula I is applied to a surface in the range of about 0.01 g/m$^2$ to about 0.45 g/m$^2$ of Formula I.

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the steps of applying a fungicidally effective amount of one or more of the compounds described below to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_{1-8}$ alkyl, $C_{3-8}$ alkenyl or $C_{3-8}$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —$SO_2$—R substituent.

The term "alkylthio" refers to an —S—R substituent.

The term "halothio" refers to a sulfur substituted with three or five F substituents.

The term "haloalkylthio" refers to an alkylthio, which is substituted with Cl, F, I, or Br or any combination thereof.

The term "alkylaminocarbonyl" refers to a —C(O)—N(H)—R substituent.

The term "trialkylsilyl" refers to —$SiR_3$.

The term "cyano" refers to a —C≡N substituent.

The term "hydroxyl" refers to an —OH substituent.

The term "amino" refers to a —$NH_2$ substituent.

The term "alkylamino" refers to a —N(H)—R substituent.

The term "dialkylamino" refers to a —$NR_2$ substituent.

The term "alkoxyalkyl" refers to an alkoxy substitution on an alkyl.

The term "halogen" or "halo" refers to one or more halogen atoms, defined as F, Cl, Br, and I.

The term "nitro" refers to a —$NO_2$ substituent.

Unless specifically noted or clearly implied otherwise the term "about" refers to a range of values of plus or minus 10 percent, e.g. about 1 refers to the range 0.9 to 1.1.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like. Additionally, the compounds of Formula I may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

It is also understood by those skilled in the art that additional substitution is allowable, unless otherwise noted, as long as the rules of chemical bonding and strain energy are satisfied and the product still exhibits fungicidal activity.

Fungicidally effective amount of the compounds include amounts sufficient to kill or control true fungi, pseudo-fungi, and related organisms including water moulds.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1. The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, N-3, 5-dichlorophenyl-succinimide, N-3-nitrophenylitaconimide, 2-(thiocyanatomethylthio)-benzothiazole, (3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, albendazole, aldimorph, allicin, allyl alcohol, ametoctradin, amisulbrom, amobam, *Ampelomyces quisqualis*, ampropylfos, anilazine, antimycin, asomate, aureofungin, azaconazole, azithiram, azoxystrobin, *Bacillus subtilis, Bacillus subtilis* strain QST713, barium polysulfide, Bayer 32394, benalaxyl, benalaxyl-M, benquinox, benodanil, benomyl, bentaluron, benthiavalicarb, benthiavalicarb-isopropyl, benthiazole, benzamacril, benzamacril-isobutyl, benzamorf, benzohydroxamic acid, benzovindiflupyr, benzylaminobenzene-sulfonate (BABS) salt, berberine, berberine chloride, bethoxazin, bicarbonates, bifujunzhi, binapacryl, biphenyl, bismerthiazol, bis(methylmercury) sulfate, bis(tributyltin) oxide, bitertanol, bithionol, bixafen, blasticidin-S, borax, Bordeaux mixture, boscalid, bromothalonil, bromuconazole, bupirimate, Burgundy mixture, buthiobate, butylamine, cadmium calcium copper zinc chromate sulfate, calcium polysulfide, *Candida oleophila*, captafol, captan, carbamorph, carbendazim, carbendazim benzenesulfonate, carbendazim sulfite, carboxin, carpropamid, carvacrol, carvone, CECA, Cheshunt mixture, chinomethionat, chitosan, chlazafenone, chlobenthiazone, chloraniformethan, chloranil, chlorfenazole, chlorodinitronaphthalenes, chlorquinox, chloroneb, chloropicrin, chlorothalonil, chlozolinate, climbazole, clotrimazole, *Coniothyrium minitans*, copper acetate, copper bis(3-phenylsalicylate), copper carbonate, basic, copper hydroxide, copper naphthenate, copper octanoate, copper oleate, copper oxychloride, copper silicate, copper sulfate, copper sulfate (tribasic), copper zinc chromate, coumoxystrobin, cresol, cufraneb, cupric hydrazinium sulfate, cuprobam, cuprous oxide, cyazofamid, cyclafuramid, cycloheximide, cyflufenamid, cymoxanil, cypendazole, cyproconazole, cyprodinil, cyprofuram, dazomet, dazomet-sodium, DBCP, debacarb, decafentin, dehydroacetic acid, diammonium ethylenebis-(dithiocarbamate), dichlofluanid, dichlonc, dichloran, dichlorophen, dichlozoline, diclobutrazol, diclocymet, diclomezine, diclomezine-sodium, diethofencarb, diethyl pyrocarbonate, difenoconazole, difenzoquat ion, diflumetorim, dimetachlone, dimethirimol, dimethomorph, dimoxystrobin, dingjunezuo, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, dithioether, DNOC, DNOC-ammonium, DNOC-potassium, DNOC-sodium, dodemorph, dodemorph acetate, dodicin, dodicin hydrochloride, dodicin-sodium, dodine, dodine free base, drazoxolon, EBP, edifenphos, enestrobin, enestroburin, enoxastrobin, epoxiconazole, ESBP, etaconazole, etem, ethaboxam, ethirim, ethirimol, ethoxyquin, ethirimol, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenaminstrobin, fenapanil, fenarimol, fenbuconazole, fenfuram, fenhexamid, fenitropan, fenjuntong, fenoxanil, fenpiclonil, fenpropidin, fenpropimorph, fenpyrazamine, fentin, fentin acetate, fentin chloride, fentin hydroxide, ferbam, ferimzone, fluazinam, fludioxonil, flufenoxystrobin, flumetover, flumorph, fluopicolide, fluopyram, fluoroimide, fluotrimazole, fluoxastrobin, fluquinconazole, flusilazole, flusulfamide, fluthiacet-methyl, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, *Fusarium oxysporum*, *Gliocladium* spp., glyodine, griseofulvin, guazatine, guazatine acetates, GY-81, halacrinate, Hercules 3944, hexachlorobenzene, hexachlorobutadiene, hexachlorophene, hexaconazole, hexylthiofos, huanjunzuo, hydrargaphen, hymexazol, ICIA0858, imazalil, imazalil nitrate, imazalil sulfate, imibenconazole, iminoctadine, iminoctadine triacetate, iminoctadine tris(albesilate), inezin, iodocarb, iodomethane, ipconazole, ipfenpyrazolone, iprobenfos, iprodione, iprovalicarb, isopamphos, isoprothiolane, isopyrazam, isotianil, isovaledione, jiaxiangjunzhi, kasugamycin, kasugamycin hydrochloride hydrate, kejunlin, kresoxim-methyl, laminarin, lvdingjunzhi, mancopper, mancozeb, mandipropamid, maneb, mebenil, mecarbinzid, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl iodide, methyl isothiocyanate, methylmercury benzoate, methylmercury dicyandiamide, methylmercury pentachlorophenoxide, metiram, metominostrobin, metrafenone, metsulfovax, mildiomycin, milneb, moroxydine, moroxydine hydrochloride, mucochloric anhydride, myclobutanil, myclozolin, N-ethylmercurio-4-toluenesulfonanilide, N-(ethylmercury)-p-toluenesulphonanilide, nabam, natamycin, nickel bis(dimethyldithiocarbamate), nitrostyrene, nitrothal-isopropyl, nuarimol, OCH, octhilinone, ofurace, oleic acid (fatty acids), orysastrobin, osthol, oxadixyl, oxathiapiprolin, oxine-copper, oxpoconazole fumarate, oxycarboxin, parinol, pefurazoate, penconazole, pencycuron, penflufen, pentachlorophenol, pentachlorophenyl laurate, penthiopyrad, phenamacril, phenylmercuriurea, phenylmercury acetate, phenylmercury chloride, phenylmercury derivative of pyrocatechol, phenylmercury dimethyldithiocarbamate, phenylmercury nitrate, phenylmercury salicylate, *Phlebiopsis gigantea*, phosdiphen, phosphonic acid, phthalide, picoxystrobin, piperalin, polycarbamate, polyoxin B, polyoxins, polyoxorim, polyoxorim-zinc, potassium azide, potassium bicarbonate, potassium hydroxyquinoline sulfate, potassium polysulfide, potassium thiocyanate, probenazole, prochloraz, prochloraz-manganese, procymidone, propamidine, propamidine dihydrochloride, propamocarb, propamocarb hydrochloride, propiconazole, propineb, proquinazid, prothiocarb, prothiocarb hydrochloride, prothioconazole, pyracarbolid, pyraclostrobin, pyrametostrobin, pyraoxystrobin, pyrazophos, pyribencarb, pyributicarb, pyridinitril, pyrifenox, pyrimethanil, pyriofenone, pyrisoxazole, pyroquilon, pyroxychlor, pyroxyfur, quinacetol, quinacetol sulfate, quinazamid, quinoclamine, quinconazole, quinoxyfen, quintozene, rabenzazole, *Reynoutria sachalinensis* extract, saisentong, salicylanilide, santonin, sedaxane, silthiofam, simeconazole, sodium 2-phenylphenoxide, sodium azide, sodium bicarbonate, sodium orthophenylphenoxide, sodium pentachlorophenoxide, sodium polysulfide, spiroxamine, *Streptomyces griseoviridis*, streptomycin, streptomycin sesquisulfate, SSF-109, sulfur, sultropen, SYP-Z048, tar oils, tebuconazole, tebufloquin, tecloftalam, tecnazene, tecoram, tetraconazole, thiabendazole, thiadifluor, thicyofen, thifluzamide, thiochlorfenphim, thiodiazole-copper, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, triclopyricarb, *Trichoderma* spp., tricyclazole, tridemorph, trifloxystrobin, triflumizole, triforine, triticonazole, uniconazole, uniconazole-P, urbacid, validamycin, valifenalate, valiphenal, vangard, vinclozolin, xiwojunan, zarilamid, zineb, zinc naphthenate, zinc thiazole, ziram, and zoxamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chiorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioatc, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-dielexine, dinoprop, dinosaur, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fencthacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, flufiprole, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxarn, thierofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA, 4-CPA-potassium, 4-CPA-sodium; 4-CPB; 4-CPP; 2,4-D, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine; 2,4-D-2-butoxypropyl, 2,4-D choline salt, 2,4-D esters and amines; 2,4-D-2-ethylhexyl, 2,4-D-3-butoxypropyl, 2,4-D-ammonium; 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium; 3,4-DA; 3,4-DB; 2,4-DEB; 2,4-DEP; 3,4-DP; 2,3,6-TBA; 2,3,6-TBA-dimethylammonium, 2,3,6-TBA-lithium, 2,3,6-TBA-potassium, 2,3,6-TBA-sodium, 2,4,5-T; 2,4,5-T-2-butoxypropyl, 2,4,5-T-2-ethylhexyl, 2,4,5-T-3-butoxypropyl; 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine; acetochlor, acifluorfen, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, benthiocarb, bentazone, bentazone-sodium, bentranil, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carboxazole, carfentrazone, carfentrazone-ethyl, CDEA, CEPC, chlomethoxyfen, chloramb en, chloramben-ammonium, chloramben-diolamine, chloramb en-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-ammonium, chlorfcnac-sodium, chlorfenprop, chlorflurazole, chlorflurenol, chlorflurenol-methyl, chloridazon, chlorimuron, chlorimuron-ethyl, chlornidine, chlomitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clacyfos, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, diallate, dicamba, dicamba-diglycolaminc, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, diclofop, diclofop-methyl, diclosulam, diethamquat, diethamquat dichloride, diethatyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphenamid, dipropetryn, diquat, diquat dibromide, disul, disul-sodium, dithioether, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, erlujixiancaoan, esprocarb, ethachlor, ethalfluralin, ethbenzamide, ethametsulfuron, ethametsulfuron-methyl, ethaprochlor, ethidimuron, ethiolate, ethion, ethiozin, ethobenzamid, etobenzamid, etofumesate, ethoxyfen, ethoxysulfuron, etinofen, etnipromid, etobenzanid, EXD, fenasulam, fenoprop, fenoprop-3-butoxypropyl, fenoprop-butometyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxaprop-P-ethyl+isoxadifen-ethyl, fenoxasulfone, fenteracol, fenthiaprop, fentrazamide, fenuron, fenuron TCA, ferrous sulfate, flamprop, flamprop-isopropyl, fenthiaprop-ethyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl, flupyrsulfuron-methyl-sodium, fluridone, flurochloridone, fluroxypyr, fluroxypyr-butometyl, fluroxypyr-meptyl, flurtamone, fluthiacet, fomesafen, fomesafen-sodium, foramsulfuron, fosamine, fosamine-ammonium, fucaojing, fucaomi, funaihecaoling, furyloxyfen, glufosinatc, glufosinatc-ammonium, glufosinate-P, glufosinate-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, herbimycin, hexachloroacetone, hexaflurate, hexazinone, huancaiwo, huangcaoling, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, ketospiradox-potassium, kuicaoxi, lactofen, lenacil, linuron, lvxiancaolin, MAA, MAMA, MCPA, esters and amines, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metam-potassium, metam-sodium, metamifop, metamitron, metazachlor, metazosulfuron, metsulfuron-methyl, metflurazon, methabenzthiazuron, methalpropalin, methazole, methiobencarb, methiopyrisulfuron, methiozolin, methiuron, methometon, methoprotryne, methoxyphenone, methyl bromide, methyl iodide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monosulfuron, monosulfuron-ester, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, paraflufen-ethyl, parafluron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prohexadione-calcium, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyrasulfotole, pyrazogyl, pyrazolynate, pyrazosulfuron, pyrazosulfuron-ethyl, pyrazoxyfen, pyribambenz-isopropyl, pyribambenz-propyl, pyribenzoxim, pyributicarb, pyriclor, pyridafol, pyridate, pyriftalid, pyriminobac, pyrimisulfan, pyrithiobac, pyrithiobac-sodium, pyrithiobac-methyl, pyroxasulfone, pyroxsulam, quinclorac, quinmerac, quinoclamine, quinonamid, quizalofop-ethyl, quizalofop, quizalofop-P, quizalofop-P-ethyl, quizalofop-P-tefuryl, rhodethanil, rimsulfuron, saflufenacil, S-metolachlor, sebuthylazine, secbumeton, sethoxydim, shuangjiaancaolin, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosate, sulfosulfuron, sulfuric acid, sulglycapin, swep, tavron, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, triafamone, tri-allate, triasulfuron, triaziflam, tribenuron, tribenuron-methyl, tricamba, triclopyr esters and amines, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, xylachlor and zuomihuanglong.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Septoria tritici*, also known as *Mycosphaerella graminicola*), apple scab (*Ventura inaequalis*), and *Cercospora* leaf spots of sugar beets (*Cercospora beticola*), leaf spots of peanut (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

Example 1: Preparation of (E)-5-fluoro-1-((4-methoxyphenyl)sulfonyl)-3-methyl-4-(methylimino)-3,4-dihydropyrimidin-2(1H)-one (F1)

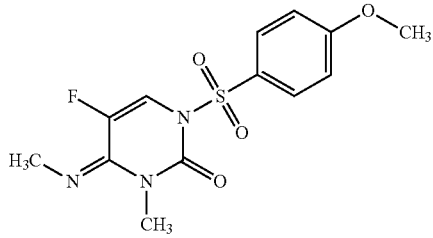

5-fluoro-4-imino-1-((4-methoxyphenyl)sulfonyl)-3,4-dihydropyrimidin-2(1H)-one (1.8 g, 6.01 mmol, prepared as described in WO 2011/017547) was stirred at room temperature in dimethylformamide (DMF, 10 mL) under a blanket of nitrogen. Anhydrous potassium carbonate ($K_2CO_3$, 1.662 g, 12.03 mmol), and iodomethane (0.562 mL, 9.02 mmol) were added. The reaction mixture was stirred at ambient temperature for 3 days (d), poured onto ice water, and extracted with ethyl acetate (EtOAc, 4×50 mL). The combined organic fractions were washed with saturated NaCl solution (100 mL), dried over anhydrous magnesium sulfate ($MgSO_4$), filtered and evaporated to yield the crude product mixture as a yellow solid (2 g). The crude mixture was purified by silica gel chromatography using a 0-100% EtOAc/hexanes gradient to provide the title compound as a white solid (0.16 g, 8.1%). Characterization data for this compound is listed in Table 2.

Example 2: Preparation of N-(5-fluoro-1-((4-methoxyphenyl)sulfonyl)-2-oxo-2,3-dihydropyrimidin-4(1H)-ylidene)acetamide

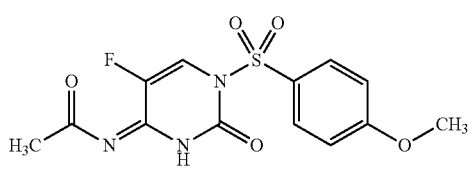 [SMILES: COc1ccc(S(=O)(=O)n2cc(F)/c(=N\C(C)=O)[nH]c2=O)cc1]

A dry 100 mL round bottom flask equipped with magnetic stirrer and nitrogen inlet was charged with 4-amino-5-fluoro-1-((4-methoxyphenyl)sulfonyl)pyrimidin-2(1H)-one (1.0 g, 3.34 mmol) and 50 mL of anhydrous acetonitrile ($CH_3CN$). To this solution was added anhydrous pyridine (0.27 mL, 3.34 mmol) followed by acetic anhydride (0.35 mL, 3.68 mmol). The reaction was stirred at ambient temperature for 17 hours (h). The reaction mixture was concentrated and the residue was chromatographed by silica gel flash chromatography eluting with a gradient of 100% hexane to 100% ethyl acetate (EtOAc). The pure fractions were combined and concentrated under vacuum on a rotary evaporator to afford N-(5-fluoro-1-((4-methoxyphenyl)sulfonyl)-2-oxo-2,3-dihydropyrimidin-4(1H)-ylidene)acetamide as a white solid (770 mg, 67.5%): $^1$H NMR (400 MHz, DMSO-$d_6$) δ 10.82 (s, 1H), 8.61 (d, J=6.1 Hz, 1H), 8.09-7.98 (m, 2H), 7.31-7.17 (m, 2H), 3.88 (s, 3H), 2.27 (s, 3H).

Example 3: Preparation of N-(5-fluoro-1-((4-methoxyphenyl)sulfonyl)-3-methyl-2-oxo-2,3-dihydropyrimidin-4(1H)-ylidene)acetamide (F31)

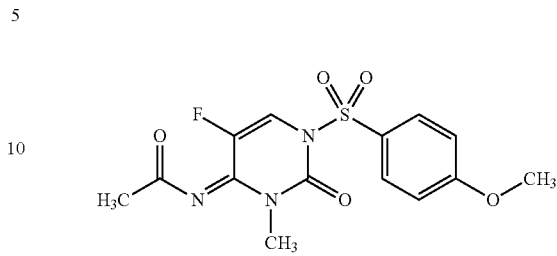

A dry 50 mL round bottom flask equipped with magnetic stirrer and nitrogen inlet was charged with N-(5-fluoro-1-((4-methoxyphenyl)sulfonyl)-2-oxo-2,3-dihydropyrimidin-4(1H)-ylidene)acetamide (0.5 g, 1.465 mmol) and 10 mL of anhydrous N,N-dimethyl formamide (DMF). To this solution was added powdered lithium carbonate (216 mg, 2.93 mmol) followed by iodomethane (182 µL, 2.93 mmol). The reaction was stirred at ambient temperature for 12 hours. Additional lithium carbonate (108 mg, 1.465 mmoles) and iodomethane (91 µL, 1.465 mmoles) were added, and the reaction was stirred at ambient temperature for another two hours. The reaction mixture was poured into 50 mL of dichloromethane ($CH_2Cl_2$, DCM), and washed with 20 mL of water and 20 mL of saturated aqueous sodium chloride solution. The organic extract was dried over anhydrous magnesium sulfate ($MgSO_4$), filtered, and concentrated under vacuum on a rotary evaporator. The resulting crude product was purified by silica gel flash chromatography eluting with a gradient of 100% hexane to 100% ethyl acetate. The pure fractions were combined and concentrated under vacuum on a rotary evaporator to afford the title compound as a white solid (298 mg, 57.2%). Characterization data for this compound is listed in Table 2.

The following compounds were prepared as described in US 2011/0263627 A1, and were used to make the compounds prepared as in Examples 4, 5 and 6:

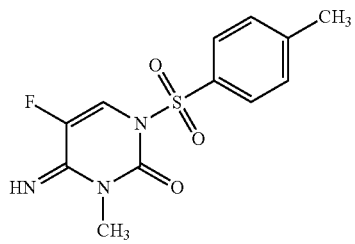 [SMILES: Cc1ccc(S(=O)(=O)n2cc(F)c(=N)n(C)c2=O)cc1]

5-fluoro-4-imino-3-methyl-1-tosyl-3,4-dihydropyrimidin-2(1H)-one (119 mg, 56%): mp 148.9-150.2° C.; $^1$H NMR (300 MHz, DMSO-$d_6$) δ 8.54 (br s, 1H), 7.99 (d, J=6.0 Hz, 1H), 7.93 (d, J=8.2 Hz, 2H), 7.49 (d, J=8.6 Hz, 2H), 3.12 (s, 3H), 2.43 (s, 3H); ESIMS m/z 297.1 ([M]

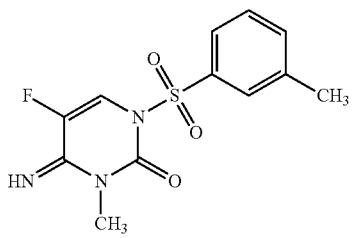 [SMILES: Cc1cccc(S(=O)(=O)n2cc(F)c(=N)n(C)c2=O)c1]

5-fluoro-4-imino-3-methyl-1-(m-tolylsulfonyl)-3,4-dihydropyrimidin-2(1H)-one (60 mg, 30%): mp 198.6-199.9° C.; $^1$H NMR (300 MHz, DMSO-d$_6$) δ 2.42 (s, 3H), 3.13 (s, 3H), 7.54-7.61 (m, 2H), 7.83-7.86 (m, 2H), 7.99 (d, J=5.9 Hz, 1H), 8.56 (br s, 1H); ESIMS m/z 297.1 ([M]$^+$).

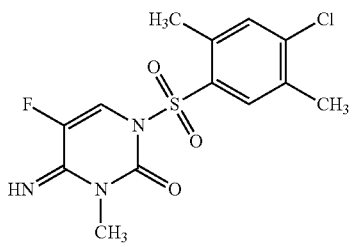 [SMILES: Cc1cc(S(=O)(=O)n2cc(F)c(=N)n(C)c2=O)c(C)cc1Cl]

1-(4-chloro-2,5-dimethylphenylsulfonyl)-5-fluoro-4-imino-3-methyl-3,4-dihydropyrimidin-2(1H)-one (53 mg, 26%): mp 145.0-147.0° C.; $^1$H NMR (300 MHz, DMSO-d$_6$) δ 8.60 (br s, 1H), 8.04 (d, J=6.2 Hz, 1H), 8.03 (s, 1H), 7.61 (s, 1H), 3.12 (s, 3H), 2.45 (s, 3H), 2.40 (s, 3H); ESIMS m/z 345.0 ([M]$^+$).

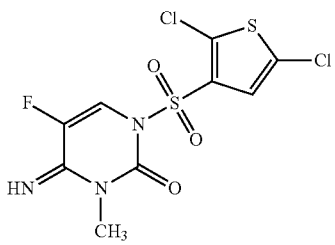 [SMILES: Cn1c(=N)c(F)cn(S(=O)(=O)c2cc(Cl)sc2Cl)c1=O]

1-(2,5-dichlorothiophen-3-ylsulfonyl)-5-fluoro-4-imino-3-methyl-3,4-dihydropyrimidin-2(1H)-one (22 mg, 11%): mp 261.1-263.4° C.; $^1$H NMR (300 MHz, DMSO-d$_6$) δ 8.70 (br s, 1H), 7.94 (d, J=5.8 Hz, 1H), 7.63 (s, 1H), 3.18 (s, 3H); ESIMS m/z 356.9 ([M]$^+$).

Example 4: Preparation of N-(5-fluoro-1-((4-methoxyphenyl)sulfonyl)-3-methyl-2-oxo-2,3-dihydropyrimidin-4(1H)-ylidene)acetamide (F31)

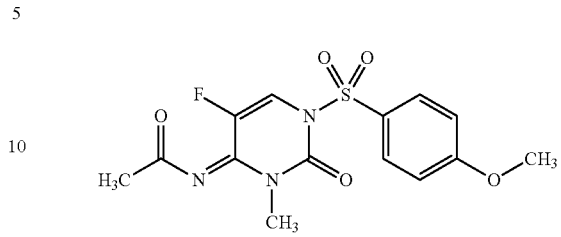

To a solution of 5-fluoro-4-imino-1-((4-methoxyphenyl)sulfonyl)-3-methyl-3,4-dihydropyrimidin-2(1H)-one (0.100 g, 0.319 mmol, prepared as described in US 2011/0263627 A1) in CH$_2$Cl$_2$ (5 ml) at 0° C. was added pyridine (0.03 mL, 0.383 mmol) followed by acetyl chloride (0.025 mL, 0.351 mmol). The reaction mixture was warmed to room temperature and stirred for 16 h. The solvent was evaporated under reduced pressure and the residue was purified by means of column chromatography on silica gel (hexanes/EtOAc, 7/3) in order to obtain the title compound as a white solid (0.077 g, 68%). Characterization data for this compound is listed in Table 2.

Example 5: Preparation of methyl (5-fluoro-1-((4-methoxyphenyl)sulfonyl)-3-methyl-2-oxo-2,3-dihydropyrimidin-4(1H)-ylidene)carbamate (F27)

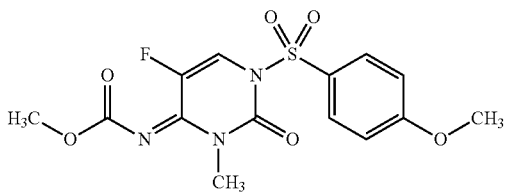

To a solution of 5-fluoro-4-imino-1-((4-methoxyphenyl)sulfonyl)-3-methyl-3,4-dihydropyrimidin-2(1H)-one (0.170 g, 0.530 mmol) in DCM (12 mL) at −10° C. was added pyridine (0.340 mL, 4.240 mmol) followed by methyl chloroformate (0.330 mL, 4.240 mmol). The reaction mixture was stirred at −10° C. for 48 h. The solvent was evaporated under reduced pressure and the residue was purified by means of column chromatography on silica gel (hexanes/EtOAc, 7/3) in order to obtain the title compound as white solid (0.080 g, 40%). Characterization data for this compound is listed in Table 2.

Example 6: Preparation of phenyl (5-fluoro-1-((4-methoxyphenyl)sulfonyl)-3-methyl-2-oxo-2,3-dihydropyrimidin-4(1H)-ylidene)carbamate (F24)

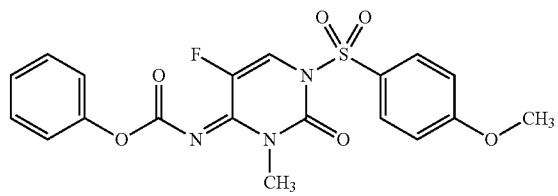 [SMILES: COc1ccc(S(=O)(=O)n2cc(F)/c(=N\C(=O)Oc3ccccc3)n(C)c2=O)cc1]

To a solution of 5-fluoro-4-imino-1-((4-methoxyphenyl)sulfonyl)-3-methyl-3,4-dihydropyrimidin-2(1H)-one (0.110 g, 0.350 mmol) in DCM (8 mL) at 0° C. was added pyridine (0.034 mL, 0.420 mmol) followed by phenyl chloroformate (0.05 mL, 0.385 mmol). The reaction mixture was warmed to room temperature and stirred for 16 h. The solvent was evaporated under reduced pressure and the residue was purified by means of column chromatography on silica gel (hexanes/EtOAc, 7/3) in order to obtain the title compound as a white solid (0.110 g, 72%). Characterization data for this compound is listed in Table 2.

Example 7: Preparation of 5-fluoro-4-((2-fluorobenzyl)imino)-1-((4-methoxyphenyl)sulfonyl)-3-methyl-3,4-dihydropyrimidin-2(1H)-one (F53)

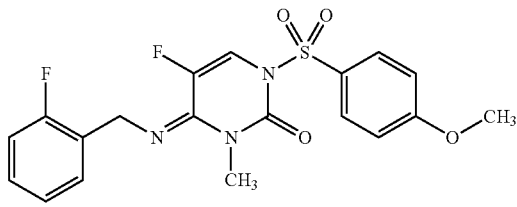 [SMILES: COc1ccc(S(=O)(=O)n2cc(F)/c(=N\Cc3ccccc3F)n(C)c2=O)cc1]

A solution of 5-fluoro-4-imino-1-((4-methoxyphenyl)sulfonyl)-3-methyl-3,4-dihydropyrimidin-2(1H)-one (0.219 g, 0.700 mmol) and potassium carbonate (0.290 g, 2.100 mmol) in 2-fluorobenzylbromide (2.5 mL, 21.0 mmol) in a sealed vial was placed in a Biotage Initiator microwave reactor for 16 h at 100° C., with external IR-sensor temperature monitoring from the side of the vessel. The reaction mixture was concentrated under vacuum and the residue was purified by means of column chromatography on silica gel (hexanes/EtOAc, 6/4) in order to obtain the title compound as an off-white solid (0.058 g, 22%). Characterization data for this compound is listed in Table 2.

Example 9: Preparation of 5-fluoro-1-(phenylsulfonyl)-3-trideuteriomethyl-4-(trideuteriomethylimino)-3,4-dihydropyrimidin-2(1H)-one (F61)

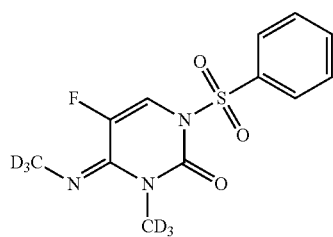 [SMILES: [2H]C([2H])([2H])/N=c1\c(F)cn(S(=O)(=O)c2ccccc2)c(=O)n1C([2H])([2H])[2H]]

To a dry suspension of 4-amino-5-fluoro-1-(phenylsulfonyl)pyrimidin-2(1H)-one (600 mg, 2.29 mmol) and lithium carbonate (333 mg, 4.51 mmol) in DMF (7 mL), was added trideuteriomethyl iodide (807 mg, 5.64 mmol). The reaction mixture was heated at 45° C. for 3.5 h. The reaction mixture was cooled to room temperature and partitioned between EtOAc (10 mL) and saturated aqueous sodium chloride solution (10 mL). The layers were separated and the aqueous fraction re-extracted with EtOAc (10 mL). The organic layers were combined, washed with brine (4×10 mL), dried (Na$_2$SO$_4$), concentrated, and the residue was purified by silica gel flash chromatography eluting with a gradient of 100% hexane to 80% ethyl acetate. The pure fractions were combined and concentrated under vacuum on a rotary evaporator to afford the title compound as a white solid (23 mg, 3.6%). Characterization data for this compound is listed in Table 2.

Example 10: Preparation of 5-fluoro-1-((4-methoxyphenyl)sulfonyl)-3-trideuteriomethyl-4-(trideuteriomethylimino)-3,4-dihydropyrimidin-2(1H)-one (F63)

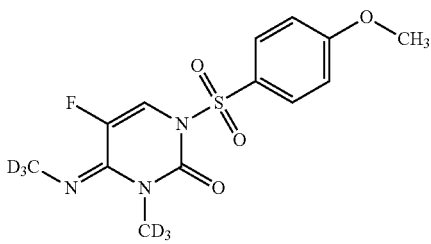

To a dry suspension of 4-amino-5-fluoro-1-((4-methoxyphenyl)sulfonyl)pyrimidin-2(1H)-one (1.11 g, 3.70 mmol) and lithium carbonate (410 mg, 5.55 mmol) in DMF (7 mL), was added trideuteriomethyl iodide (1.36 g, 9.40 mmol). The reaction mixture was heated at 50° C. for 2 h. The reaction mixture was cooled to room temperature and partitioned between EtOAc (10 mL) and saturated aqueous sodium chloride solution (10 mL). The layers were separated and the aqueous fraction re-extracted with EtOAc (10 mL). The organic layers were combined, washed with brine (4×10 mL), dried (Na$_2$SO$_4$), concentrated, and the residue was purified by silica gel flash chromatography eluting with a gradient of 100% hexane to 80% ethyl acetate. The pure fractions were combined and concentrated under vacuum on a rotary evaporator to afford the title compound as a white solid (15 mg, 2.5%). Characterization data for this compound is listed in Table 2.

Example 11: Preparation of 5-fluoro-1-((4-methylphenyl)sulfonyl)-3-trideuteriomethyl-4-(trideuteriomethylimino)-3,4-dihydropyrimidin-2(1H)-one (F62)

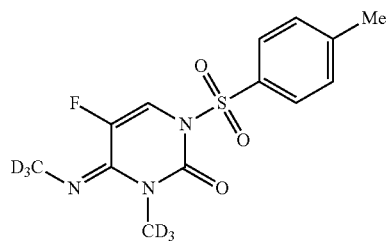 [SMILES: [2H]C([2H])([2H])/N=c1\c(F)cn(S(=O)(=O)c2ccc(C)cc2)c(=O)n1C([2H])([2H])[2H]]

To a dry suspension of 4-amino-5-fluoro-1-((4-methylphenyl)sulfonyl)pyrimidin-2(1H)-one (322 mg, 2.22 mmol) and lithium carbonate (333 mg, 4.51 mmol) in DMF (7 mL), was added trideuteriomethyl iodide (5.64 mmol, 807 mg). The reaction mixture was heated at 50° C. for 4 h. The reaction mixture was cooled to room temperature and partitioned between EtOAc (10 mL) and saturated aqueous sodium chloride solution (10 mL). The layers were separated and the aqueous fraction re-extracted with EtOAc (10 mL). The organic layers were combined, washed with brine (4×10 mL), dried (Na$_2$SO$_4$), concentrated, and the residue was purified by silica gel flash chromatography eluting with a gradient of 100% hexane to 80% ethyl acetate. The pure fractions were combined and concentrated under vacuum on a rotary evaporator to afford the title compound as a white solid (10 mg, 1.5% yield). Characterization data for this compound is listed in Table 2.

Example 12: Preparation of (E)-N-(3-benzoyl-5-fluoro-2-oxo-1-tosyl-2,3-dihydropyrimidin-4(1H)-ylidene)benzamide (F37)

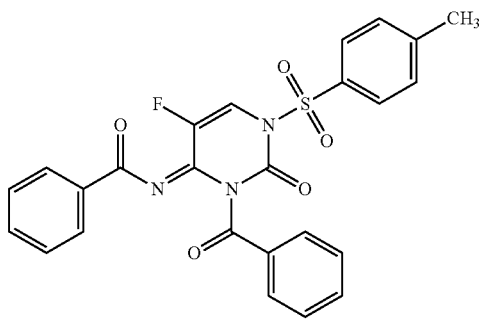 [SMILES: Cc1ccc(S(=O)(=O)n2cc(F)/c(=N\C(=O)c3ccccc3)n(C(=O)c3ccccc3)c2=O)cc1]

A suspension of 4-amino-5-fluoro-1-tosylpyrimidin-2(1H)-one (500 mg, 1.77 mmol), triethylamine (714 mg, 7.06 mmol) and dioxane (2.5 ml) was stirred at room temperature. Benzoyl chloride (0.40 ml, 3.4 mmol) was added dropwise, giving the mixture a light reddish cast. The reaction was stirred overnight at room temperature. The dark brown mixture was diluted with water and extracted with dichloromethane. The combined organic layers were dried over sodium sulfate, and concentrated. The residue was purified by normal phase chromatography (gradient, 10 to 60% EtOAC/hexane) and triturated in ethyl acetate to provide the title compound as an off white solid (278 mg, 32%). Characterization data for this compound is listed in Table 2.

Example 13: Preparation of (5-fluoro-3-(hydroxymethyl)-4-imino-1-tosyl-3,4-dihydropyrimidin-2(1H)-one

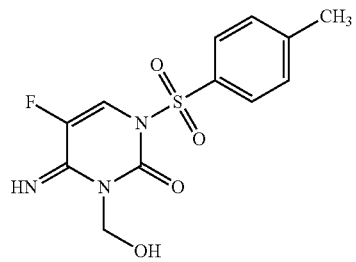 [SMILES: Cc1ccc(S(=O)(=O)n2cc(F)c(=N)n(CO)c2=O)cc1]

A 500 mL round-bottomed flask equipped with a magnetic stir bar was charged with 33% aqueous formaldehyde (20 g, 246 mmol), 4-amino-5-fluoro-1-tosylpyrimidin-2(1H)-one (10 g, 35.3 mmol) and distilled water (200 mL) to give a white suspension. The mixture was stirred under nitrogen at reflux for 3 hours. The mixture was cooled and filtered. The filter cake was washed with 25 mL of water and air dried for five minutes to yield the title compound as a white solid (2.2 g, 22%): $^1$H NMR (400 MHz, DMSO-d$_6$) δ 9.28 (t, J=6.1 Hz, 1H), 8.35 (d, J=6.6 Hz, 1H), 7.95-7.84 (m, 2H), 7.50-7.41 (m, 2H), 5.95 (t, J=6.9 Hz, 1H), 4.72 (t, J=6.4 Hz, 2H), 2.41 (s, 3H); $^{13}$C NMR (101 MHz, DMSO-d$_6$) δ 156.16 (d, J=15.1 Hz), 149.21, 145.64, 137.99, 135.51, 133.56, 129.24 (d, J=63.5 Hz), 123.83 (d, J=35.3 Hz), 63.32, 21.13; $^{19}$F NMR (376 MHz, DMSO-d$_6$) δ −164.79.

Example 14: Preparation of 5-fluoro-4-imino-3-(methoxymethyl)-1-tosyl-3,4-dihydropyrimidin-2(1H)-one

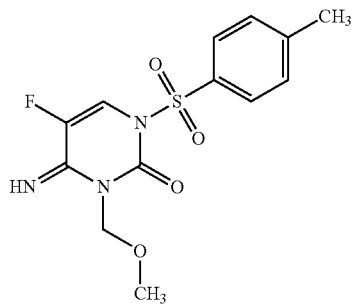 [SMILES: COCn1c(=N)c(F)cn(S(=O)(=O)c2ccc(C)cc2)c1=O]

In a 4 mL vial equipped with a magnetic stir bar charged with Deoxyfluor® (50% in THF, 900 mg, 2.0 mmol) was added 5-fluoro-3-(hydroxymethyl)-4-imino-1-tosyl-3,4-dihydropyrimidin-2(1H)-one (140 mg, 0.45 mmol). After stirring for two minutes the suspension transformed into an orange solution, which was stirred for an additional 30 minutes. The solution was cooled to 0° C. and was quenched by careful addition of methanol (1 mL). The solution was concentrated under a stream of nitrogen gas and the resulting residue was purified by silica gel chromatography, eluting with a solvent gradient of 0 to 100% EtOAc in hexanes to furnish the title compound as a colorless oil (14 mg, 9%): $^1$H NMR (400 MHz, acetone-d$_6$) δ 8.37 (s, 1H), 8.26 (d, J=6.5 Hz, 1H), 8.02-7.95 (m, 2H), 7.50-7.41 (m, 2H), 4.90-4.82 (m, 2H), 3.29 (s, 3H), 2.45 (s, 3H); $^{13}$C NMR (101 MHz, acetone-d$_6$) δ 158.52 (d, J=14.7 Hz), 150.26, 146.86, 139.16 (d, J=3.7 Hz), 136.71, 134.98, 130.38 (d, J=17.5 Hz), 124.79 (d, J=35.6 Hz), 72.49 (d, J=12.2 Hz), 56.45, 21.60; ESIMS m/z 328 ([M+H]$^+$), 326 ([M−H]$^-$).

Example 15: Preparation of Z)-(5-fluoro-6-(isobutyrylimino)-2-oxo-3-tosyl-2,3-dihydropyrimidin-1(6H)-yl)methyl isobutyrate (F25)

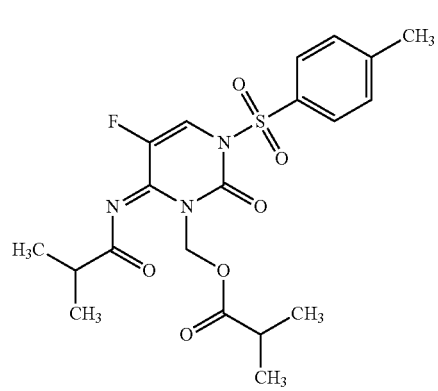 [SMILES: Cc1ccc(S(=O)(=O)n2cc(F)/c(=N/C(=O)C(C)C)n(COC(=O)C(C)C)c2=O)cc1]

A solution of the mixture containing 5-fluoro-3-(hydroxymethyl)-4-imino-1-tosyl-3,4-dihydropyrimidin-2(1H)-one (250 mg of mixture, 0.23 mmol), N,N-diisopropylethylamine (307 mg, 2.37 mmol) and 4-dimethylaminopyridine (48 mg, 0.40 mmol) in dichloromethane (6 ml) was stirred at room temperature. Isobutyryl chloride (91 μL, 0.87 mmol) was added and the solution was stirred overnight at room temperature. The reaction mixture was concentrated and purification of the residue by normal phase chromatography (gradient, 0 to 60% EtOAc/hexane) provided the title compound as an off-white foam (74 mg, 70%). Characterization data for this compound is listed in Table 2.

Example 16: Evaluation of Fungicidal Activity: Leaf Blotch of Wheat (*Mycosphaerella graminicola*; anamorph: *Septoria tritici*; Bayer code SEPTTR)

Wheat plants (variety *Yuma*) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse for disease to develop.

The following tables present the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

TABLE 1

Compound Structures and Preparation

| No. | Structure | Appearance | Prepared as in Example: |
|---|---|---|---|
| F1 | 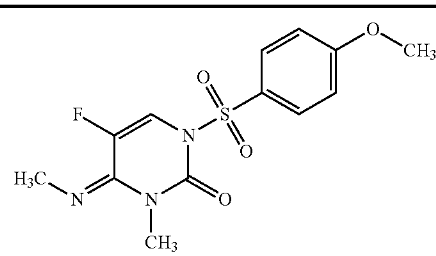 | Off white solid | 1 |
| F2 | 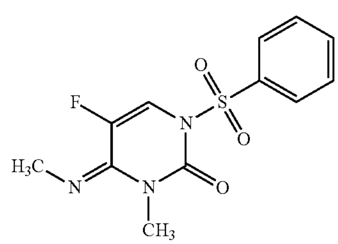 | White crystalline solid | 1 |
| F3 | 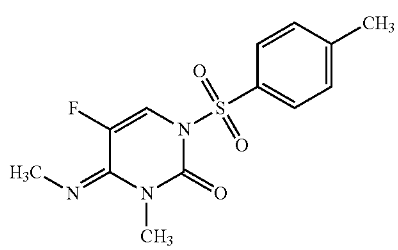 | White solid | 1 |
| F4 | 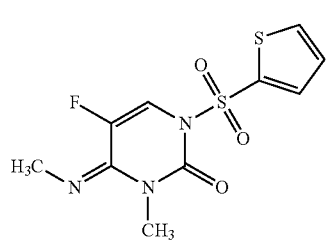 [SMILES: C/N=c1\c(F)cn(S(=O)(=O)c2cccs2)c(=O)n1C] | White solid | 1 |

TABLE 1-continued

Compound Structures and Preparation

| No. | Structure | Appearance | Prepared as in Example: |
|---|---|---|---|
| F5 | 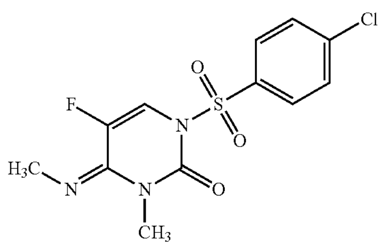 [SMILES: C/N=c1\c(F)cn(S(=O)(=O)c2ccc(Cl)cc2)c(=O)n1C] | White solid | 1 |
| F6 | 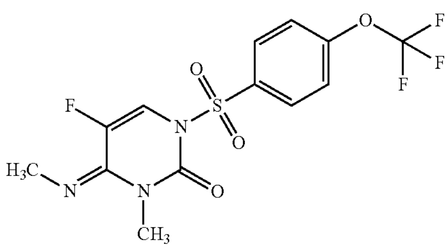 [SMILES: C/N=c1\c(F)cn(S(=O)(=O)c2ccc(OC(F)(F)F)cc2)c(=O)n1C] | White solid | 1 |
| F7 | 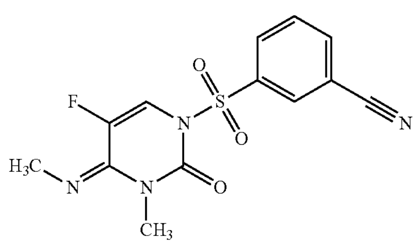 [SMILES: C/N=c1\c(F)cn(S(=O)(=O)c2cccc(C#N)c2)c(=O)n1C] | White solid | 1 |
| F8 | 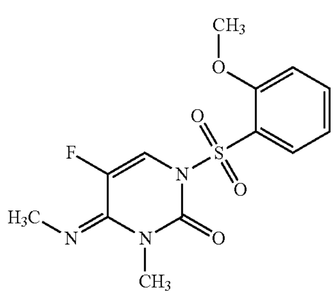 [SMILES: C/N=c1\c(F)cn(S(=O)(=O)c2ccccc2OC)c(=O)n1C] | White solid | 1 |
| F9 | 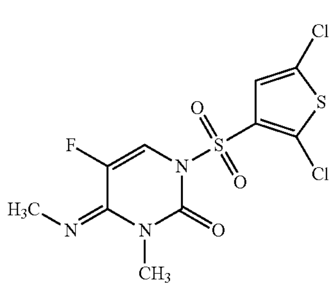 [SMILES: C/N=c1\c(F)cn(S(=O)(=O)c2cc(Cl)sc2Cl)c(=O)n1C] | White solid | 1 |

TABLE 1-continued

Compound Structures and Preparation

| No. | Structure | Appearance | Prepared as in Example: |
|---|---|---|---|
| F10 | 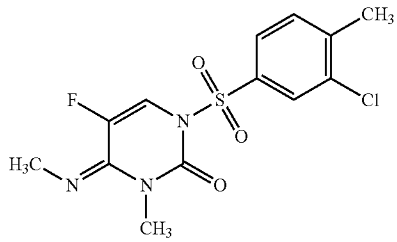 [SMILES: C/N=c1\c(F)cn(S(=O)(=O)c2ccc(C)c(Cl)c2)c(=O)n1C] | White solid | 1 |
| F11 | 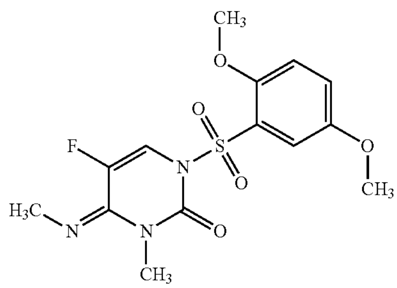 | White solid | 1 |
| F12 | 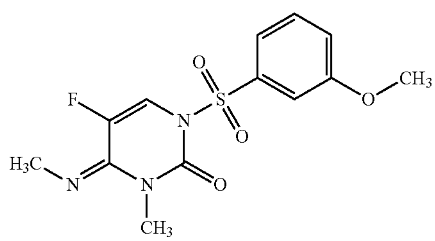 | White solid | 1 |
| F13 | 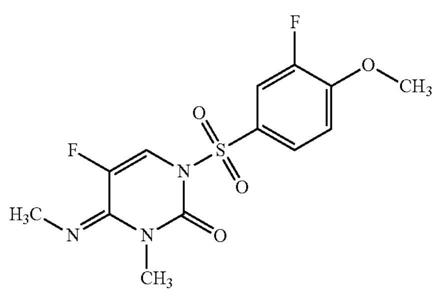 | White solid | 1 |
| F14 | 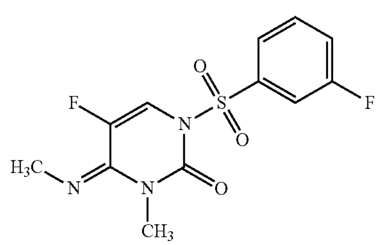 [SMILES: C/N=c1\c(F)cn(S(=O)(=O)c2cccc(F)c2)c(=O)n1C] | White solid | 1 |

TABLE 1-continued

Compound Structures and Preparation

| No. | Structure | Appearance | Prepared as in Example: |
|---|---|---|---|
| F15 | 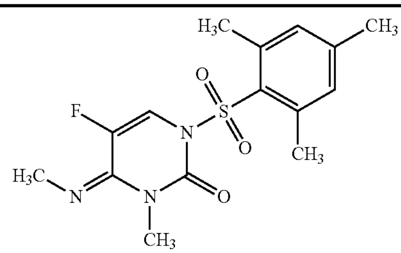 | White solid | 1 |
| F16 | 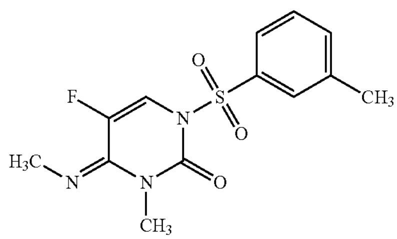 | White solid | 1 |
| F17 | 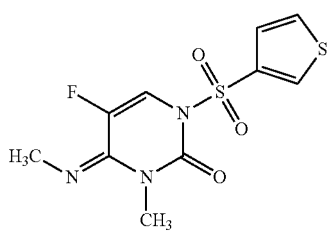 [SMILES: C/N=c1\c(F)cn(S(=O)(=O)c2ccsc2)c(=O)n1C] | White solid | 1 |
| F18 | 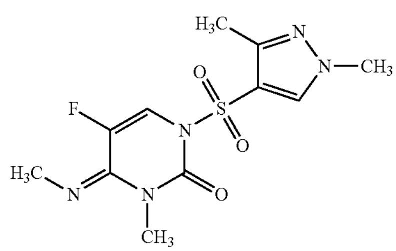 | White solid | 1 |
| F19 | 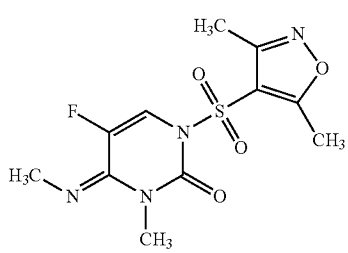 [SMILES: C/N=c1\c(F)cn(S(=O)(=O)c2c(C)noc2C)c(=O)n1C] | White solid | 1 |
| F20 | 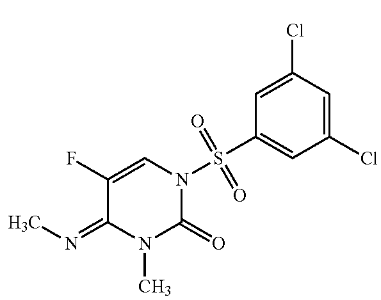 [SMILES: C/N=c1\c(F)cn(S(=O)(=O)c2cc(Cl)cc(Cl)c2)c(=O)n1C] | White solid | 1 |

TABLE 1-continued

Compound Structures and Preparation

| No. | Structure | Appearance | Prepared as in Example: |
|---|---|---|---|
| F21 | 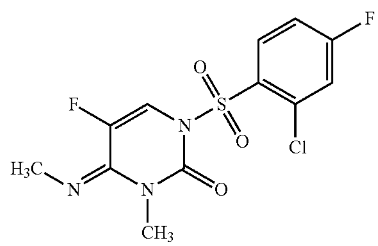 [SMILES: C/N=c1\c(F)cn(S(=O)(=O)c2ccc(F)cc2Cl)c(=O)n1C] | White solid | 1 |
| F22 | 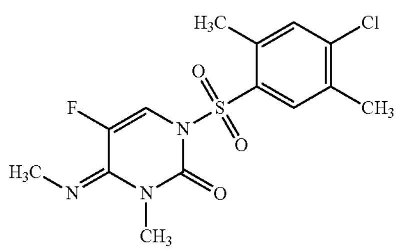 | White solid | 1 |
| F23 | 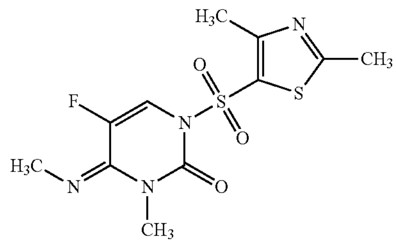 | Yellow, gummy oil | 1 |
| F24 | 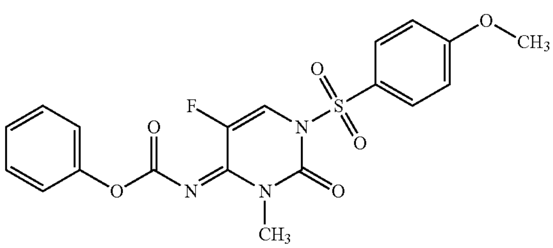 [SMILES: COc1ccc(S(=O)(=O)n2cc(F)/c(=N\C(=O)Oc3ccccc3)n(C)c2=O)cc1] | White solid | 6 |
| F25 | 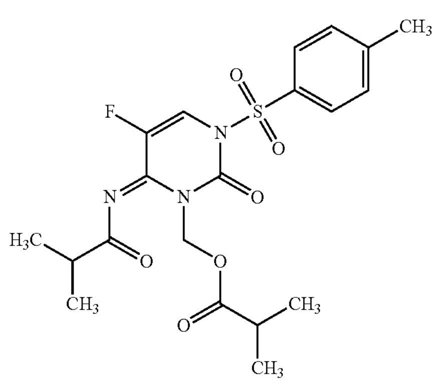 [SMILES: Cc1ccc(S(=O)(=O)n2cc(F)/c(=N/C(=O)C(C)C)n(COC(=O)C(C)C)c2=O)cc1] | Off-white foam | 15 |

TABLE 1-continued

Compound Structures and Preparation

| No. | Structure | Appearance | Prepared as in Example: |
|---|---|---|---|
| F26 | 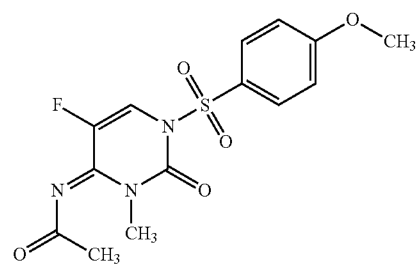 [SMILES: COc1ccc(S(=O)(=O)n2cc(F)/c(=N/C(C)=O)n(C)c2=O)cc1] | White solid | 3 and 4 |
| F27 | 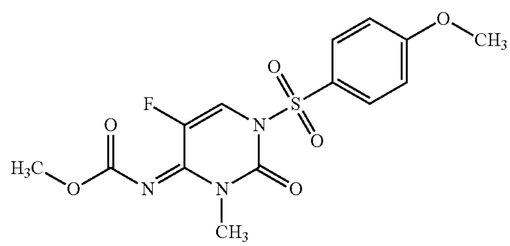 | White solid | 5 |
| F28 | 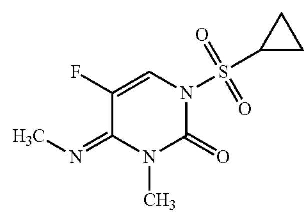 [SMILES: C/N=c1\c(F)cn(S(=O)(=O)C2CC2)c(=O)n1C] | White solid | 1 |
| F29 | 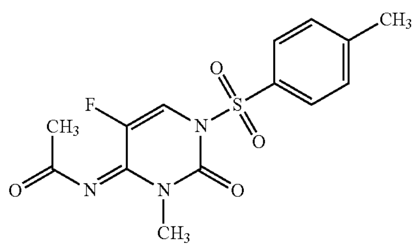 [SMILES: CC(=O)/N=c1\c(F)cn(S(=O)(=O)c2ccc(C)cc2)c(=O)n1C] | White solid | 3 and 4 |
| F30 | 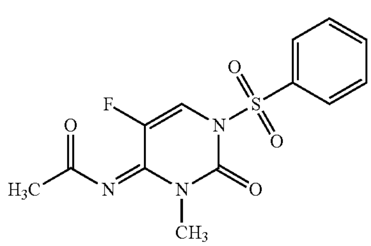 [SMILES: CC(=O)/N=c1\c(F)cn(S(=O)(=O)c2ccccc2)c(=O)n1C] | White solid | 3 and 4 |
| F31 | 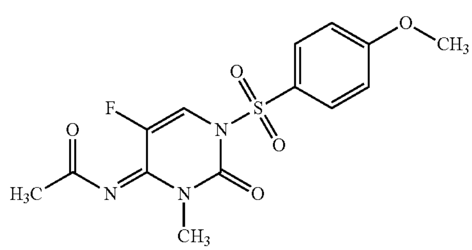 [SMILES: COc1ccc(S(=O)(=O)n2cc(F)/c(=N\C(C)=O)n(C)c2=O)cc1] | White solid | 3 and 4 |

TABLE 1-continued

Compound Structures and Preparation

| No. | Structure | Appearance | Prepared as in Example: |
|---|---|---|---|
| F32 | 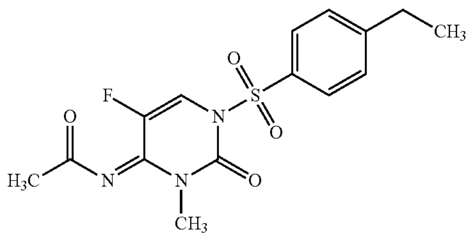 [SMILES: CCc1ccc(S(=O)(=O)n2cc(F)/c(=N\C(C)=O)n(C)c2=O)cc1] | White solid | 3 and 4 |
| F33 | 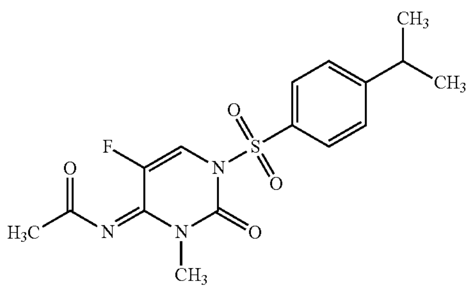 [SMILES: CC(=O)/N=c1\c(F)cn(S(=O)(=O)c2ccc(C(C)C)cc2)c(=O)n1C] | Off-white solid | 3 and 4 |
| F34 | 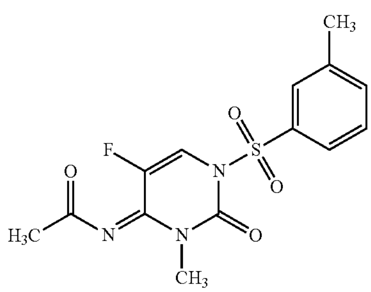 [SMILES: CC(=O)/N=c1\c(F)cn(S(=O)(=O)c2cccc(C)c2)c(=O)n1C] | White solid | 3 and 4 |
| F35 | 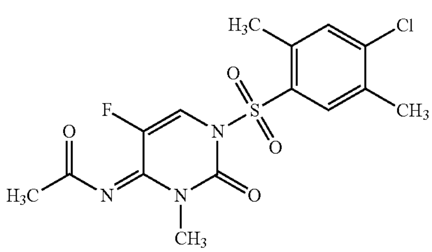 [SMILES: CC(=O)/N=c1\c(F)cn(S(=O)(=O)c2cc(C)c(Cl)cc2C)c(=O)n1C] | White solid | 3 and 4 |
| F36 | 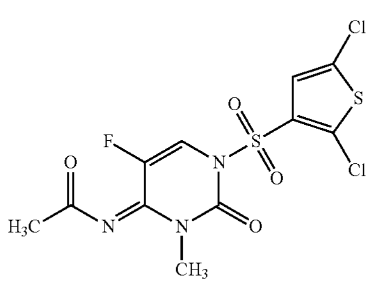 [SMILES: CC(=O)/N=c1\c(F)cn(S(=O)(=O)c2cc(Cl)sc2Cl)c(=O)n1C] | Off-white solid | 3 and 4 |

TABLE 1-continued

Compound Structures and Preparation

| No. | Structure | Appearance | Prepared as in Example: |
|---|---|---|---|
| F37 | 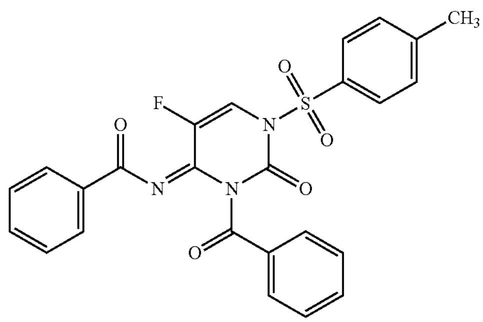 [SMILES: Cc1ccc(S(=O)(=O)n2cc(F)/c(=N\C(=O)c3ccccc3)n(C(=O)c3ccccc3)c2=O)cc1] | Off-white solid | 12 |
| F38 | 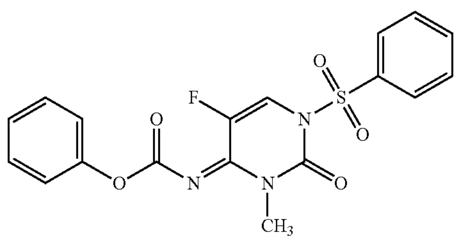 [SMILES: Cn1c(=O)n(S(=O)(=O)c2ccccc2)cc(F)/c1=N\C(=O)Oc1ccccc1] | White solid | 6 |
| F39 | 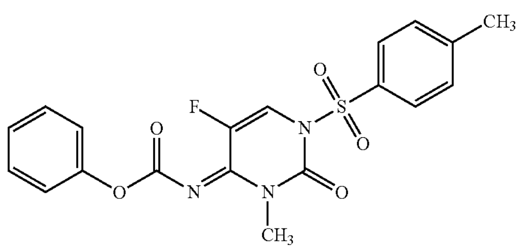 [SMILES: Cc1ccc(S(=O)(=O)n2cc(F)/c(=N\C(=O)Oc3ccccc3)n(C)c2=O)cc1] | White solid | 6 |
| F40 | 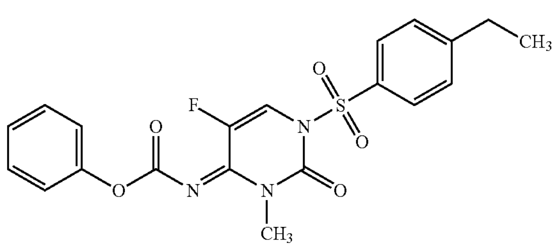 [SMILES: CCc1ccc(S(=O)(=O)n2cc(F)/c(=N\C(=O)Oc3ccccc3)n(C)c2=O)cc1] | White solid | 6 |
| F41 | 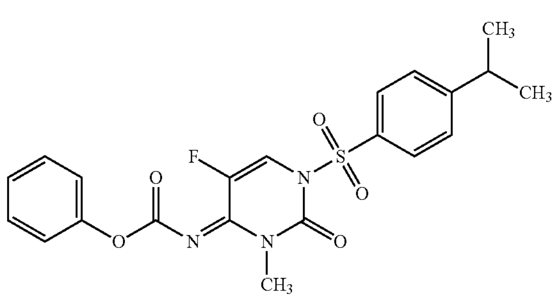 [SMILES: CC(C)c1ccc(S(=O)(=O)n2cc(F)/c(=N\C(=O)Oc3ccccc3)n(C)c2=O)cc1] | White solid | 6 |

TABLE 1-continued

Compound Structures and Preparation

| No. | Structure | Appearance | Prepared as in Example: |
|---|---|---|---|
| F42 | 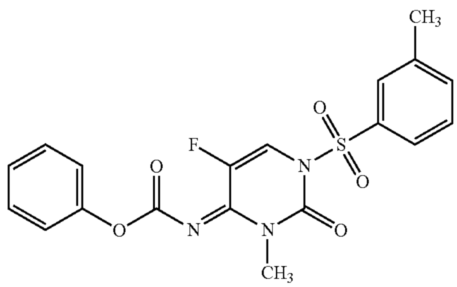 [SMILES: Cc1cccc(S(=O)(=O)n2cc(F)/c(=N\C(=O)Oc3ccccc3)n(C)c2=O)c1] | White solid | 6 |
| F43 | 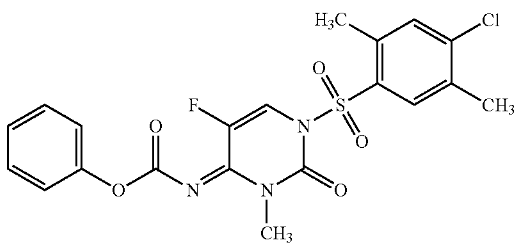 [SMILES: Cc1cc(S(=O)(=O)n2cc(F)/c(=N\C(=O)Oc3ccccc3)n(C)c2=O)c(C)cc1Cl] | White solid | 6 |
| F44 | 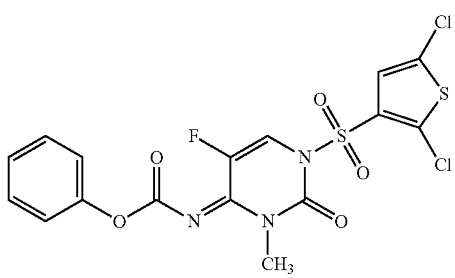 [SMILES: Cn1c(=O)n(S(=O)(=O)c2cc(Cl)sc2Cl)cc(F)/c1=N\C(=O)Oc1ccccc1] | White solid | 6 |
| F45 | 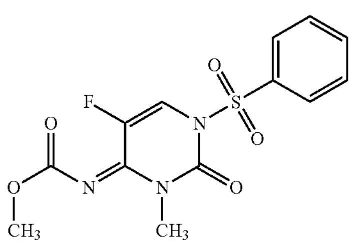 [SMILES: COC(=O)/N=c1\c(F)cn(S(=O)(=O)c2ccccc2)c(=O)n1C] | White solid | 5 |
| F46 | 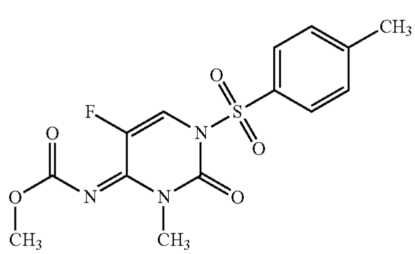 [SMILES: COC(=O)/N=c1\c(F)cn(S(=O)(=O)c2ccc(C)cc2)c(=O)n1C] | White solid | 5 |

TABLE 1-continued

Compound Structures and Preparation

| No. | Structure | Appearance | Prepared as in Example: |
|---|---|---|---|
| F47 | 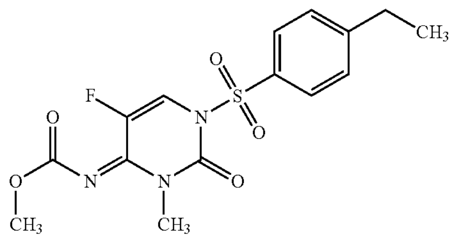 [SMILES: CCc1ccc(S(=O)(=O)n2cc(F)/c(=N\C(=O)OC)n(C)c2=O)cc1] | White solid | 5 |
| F48 | 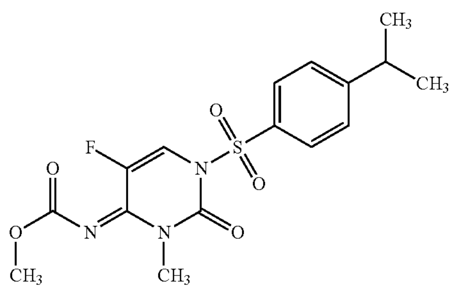 [SMILES: COC(=O)/N=c1\c(F)cn(S(=O)(=O)c2ccc(C(C)C)cc2)c(=O)n1C] | White solid | 5 |
| F49 | 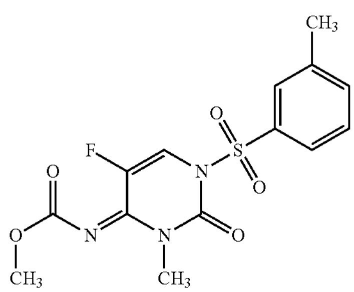 [SMILES: COC(=O)/N=c1\c(F)cn(S(=O)(=O)c2cccc(C)c2)c(=O)n1C] | White solid | 5 |
| F50 | 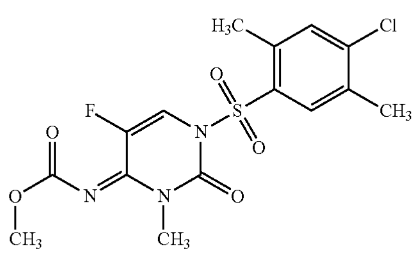 [SMILES: COC(=O)/N=c1\c(F)cn(S(=O)(=O)c2cc(C)c(Cl)cc2C)c(=O)n1C] | White solid | 5 |
| F51 | 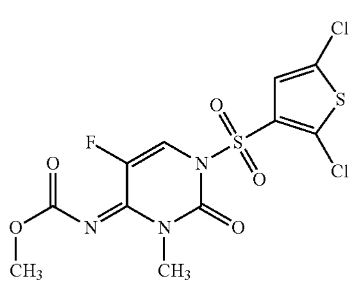 [SMILES: COC(=O)/N=c1\c(F)cn(S(=O)(=O)c2cc(Cl)sc2Cl)c(=O)n1C] | White solid | 5 |

TABLE 1-continued

Compound Structures and Preparation

| No. | Structure | Appearance | Prepared as in Example: |
|---|---|---|---|
| F52 | 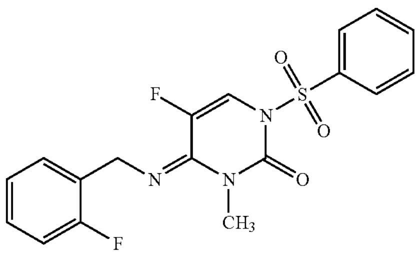 [SMILES: Cn1c(=O)n(S(=O)(=O)c2ccccc2)cc(F)/c1=N\Cc1ccccc1F] | White solid | 7 |
| F53 | 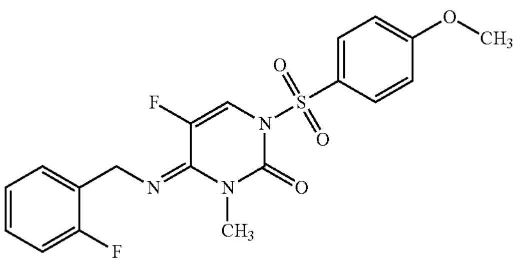 [SMILES: COc1ccc(S(=O)(=O)n2cc(F)/c(=N\Cc3ccccc3F)n(C)c2=O)cc1] | Off-white solid | 7 |
| F54 | 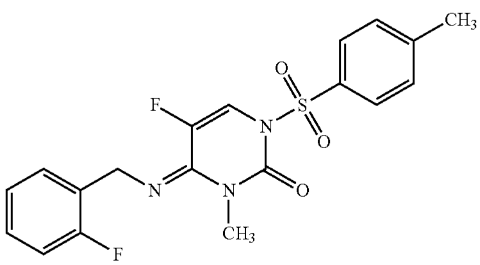 [SMILES: Cc1ccc(S(=O)(=O)n2cc(F)/c(=N\Cc3ccccc3F)n(C)c2=O)cc1] | Off-white solid | 7 |
| F55 | 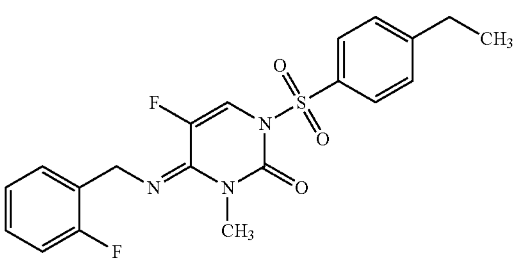 [SMILES: CCc1ccc(S(=O)(=O)n2cc(F)/c(=N\Cc3ccccc3F)n(C)c2=O)cc1] | White solid | 7 |
| F56 | 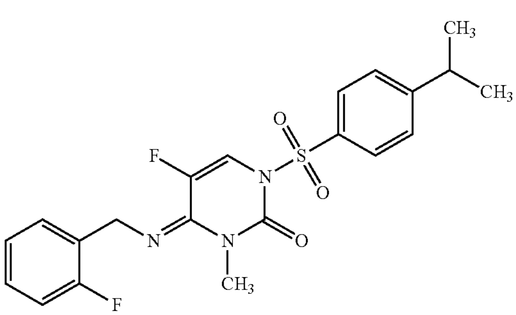 [SMILES: CC(C)c1ccc(S(=O)(=O)n2cc(F)/c(=N\Cc3ccccc3F)n(C)c2=O)cc1] | White solid | 7 |

TABLE 1-continued

Compound Structures and Preparation

| No. | Structure | Appearance | Prepared as in Example: |
|---|---|---|---|
| F57 | 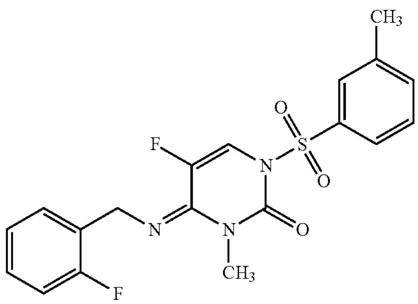 [SMILES: Cc1cccc(S(=O)(=O)n2cc(F)/c(=N\Cc3ccccc3F)n(C)c2=O)c1] | White solid | 7 |
| F58 | 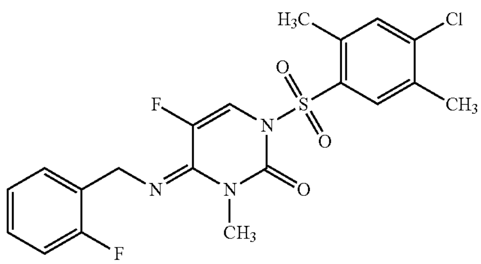 [SMILES: Cc1cc(S(=O)(=O)n2cc(F)/c(=N\Cc3ccccc3F)n(C)c2=O)c(C)cc1Cl] | White solid | 7 |
| F59 | 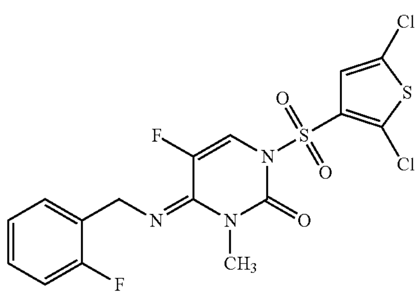 [SMILES: Cn1c(=O)n(S(=O)(=O)c2cc(Cl)sc2Cl)cc(F)/c1=N\Cc1ccccc1F] | Off-white solid | 7 |
| F61 | 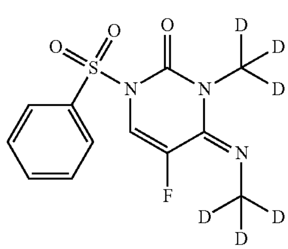 [SMILES: [2H]C([2H])([2H])/N=c1\c(F)cn(S(=O)(=O)c2ccccc2)c(=O)n1C([2H])([2H])[2H]] | White solid | 9 |
| F62 | 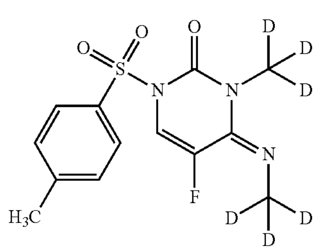 [SMILES: [2H]C([2H])([2H])/N=c1\c(F)cn(S(=O)(=O)c2ccc(C)cc2)c(=O)n1C([2H])([2H])[2H]] | White solid | 11 |

TABLE 1-continued

Compound Structures and Preparation

| No. | Structure | Appearance | Prepared as in Example: |
|---|---|---|---|
| F63 | (structure) | White solid | 10 |

TABLE 2

Analytical Data for Compounds in Table 1

| No. | Mp (° C.) | ESIMS m/z | $^1$H NMR (δ)$^a$ | $^{13}$C NMR or $^{19}$F NMR (δ) |
|---|---|---|---|---|
| F1 | 97-105 | 328 ([M + H]$^+$) | $^1$H NMR (300 MHz, CDCl$_3$) δ 8.02-7.95 (m, 2H), 7.64 (d, J = 9.2 Hz, 1H), 7.05-6.97 (m, 2H), 3.89 (s, 3H), 3.43 (d, J = 5.8 Hz, 3H), 3.17 (s, 3H) | $^{19}$F NMR (376 MHz, CDCl$_3$) δ −155.06 (dq, J = 5.83, 9.35) |
| F2 | 142-144 | — | 8.16-7.92 (m, 2H), 7.81-7.42 (m, 4H), 3.45 (d, J = 5.8 Hz, 3H), 3.17 (s, 3H) | $^{19}$F NMR (376 MHz, CDCl$_3$) δ −154.56; $^{13}$C NMR (101 MHz, CDCl$_3$) δ 146.89, 142.52, 141.62, 141.38, 140.08, 136.94, 134.76, 129.15, 115.21, 114.79, 36.31, 30.05 |
| F3 | 117-123 | — | 8.07-7.79 (m, 2H), 7.65 (d, J = 9.2 Hz, 1H), 7.45-7.30 (m, 2H), 3.44 (d, J = 5.8 Hz, 3H), 3.16 (s, 3H), 2.46 (s, 3H) | $^{13}$C NMR (101 MHz, CDCl$_3$) δ 146.95, 146.17, 142.43, 141.73, 141.49, 139.99, 133.89, 129.72, 129.27, 115.32, 114.90, 77.34, 77.23, 77.02, 76.71, 36.35, 36.23, 30.04, 21.80; $^{19}$F NMR (376 MHz, CDCl$_3$) δ −154.83, −154.84 |
| F4 | 136-138 | HRMS-FAB (m/z) [M+]$^+$ calcd for C$_{10}$H$_{10}$FN$_3$O$_3$S$_2$ 303.1, found, 304 | 7.99 (dd, J = 3.9, 1.4 Hz, 1H), 7.78 (dd, J = 5.0, 1.4 Hz, 1H), 7.60 (d, J = 9.1 Hz, 1H), 7.16 (dd, J = 5.0, 3.9 Hz, 1H), 3.45 (d, J = 5.8 Hz, 3H), 3.23 (s, 3H) | $^{13}$C NMR (101 MHz, CDCl$_3$) δ 137.18, 136.17, 135.77, 127.53, 115.14, 114.72, 36.27, 30.12 |
| F5 | 130-134 | 332 ([M + H]$^+$) | (DMSO-d$_6$) δ 8.11-8.02 (m, 2H), 7.96 (d, J = 9.6 Hz, 1H), 7.80-7.72 (m, 2H), 3.36 (s, 3H), 3.30 (s, 3H) | $^{13}$C NMR (DMSO-d$_6$) δ 146.24, 142.16, 141.48, 141.21, 140.10, 135.33, 130.73, 129.50, 115.88, 115.46, 35.86, 29.68 |
| F6 | 139.2-140.0 | 382 ([M + H]$^+$) | 8.25-8.02 (m, 2H), 7.62 (d, J = 9.1 Hz, 1H), 7.38 (dd, J = 8.9, 0.8 Hz, 2H), 3.45 (d, J = 5.8 Hz, 3H), 3.18 (s, 3H) | $^{13}$C NMR (CDCl$_3$) δ 153.68, 146.87, 141.37, 140.20, 134.80, 131.78, 121.44, 120.53, 118.85, 114.91, 114.49, 36.40, 30.10; $^{19}$F NMR (CDCl$_3$) δ −57.60, −154.56 |

TABLE 2-continued

Analytical Data for Compounds in Table 1

| No. | Mp (° C.) | ESIMS m/z | $^1$H NMR (δ)[a] | $^{13}$C NMR or $^{19}$F NMR (δ) |
|---|---|---|---|---|
| F7 | 148.6-150.6 | 323 ([M + H]$^+$) | 8.36-8.28 (m, 2H), 8.00-7.93 (m, 1H), 7.74 (dd, J = 8.7, 7.9 Hz, 1H), 7.61 (d, J = 8.9 Hz, 1H), 3.46 (d, J = 5.7 Hz, 3H), 3.17 (s, 3H) | $^{13}$C NMR (CDCl$_3$) δ 146.76, 142.82, 141.05, 138.61, 137.62, 133.43, 132.78, 130.08, 116.62, 114.58, 37.82, 36.43, 30.13 $^{19}$F NMR (CDCl$_3$) δ −153.18 |
| F8 | 204.0-205.4 | 328 ([M + H]$^+$) | 8.14 (dd, J = 8.0, 1.7 Hz, 1H), 7.70-7.60 (m, 2H), 7.19-7.11 (m, 1H), 7.05-6.98 (m, 1H), 3.93 (s, 3H), 3.45 (d, J = 13.2 Hz, 3H), 3.17 (s, 3H) | $^{13}$C NMR (CDCl$_3$) δ 156.79, 147.00, 141.98, 141.76, 139.34, 136.62, 132.70, 124.80, 120.83, 116.87, 116.45, 112.30, 56.47, 36.38, 36.26, 29.96 |
| F9 | 157.1-158.0 | 373 ([M + H]$^+$) | 7.60 (d, J = 8.9 Hz, 1H), 7.36 (s, 1H), 3.48 (d, J = 5.7 Hz, 3H), 3.23 (s, 3H) | $^{13}$C NMR (CDCl$_3$) δ 146.92, 142.31, 141.17, 139.86, 133.28, 132.81, 127.88, 115.28, 36.44, 30.13; $^{19}$F NMR (CDCl$_3$) δ −153.97 |
| F10 | 149.4-151.0 | 346 ([M + H]$^+$) | 7.98 (d, J = 2.0 Hz, 1H), 7.87 (dd, J = 8.1, 2.0 Hz, 1H), 7.62 (d, J = 9.1 Hz, 1H), 7.44 (d, J = 8.1 Hz, 1H), 3.45 (d, J = 5.8 Hz, 3H), 3.38 (s, 3H), 3.18 (s, 3H), 2.46 (s, 3H) | $^{13}$C NMR (CDCl$_3$) δ 146.84, 144.20, 142.57, 141.48, 135.59, 131.34, 129.34, 128.56, 127.59, 126.35, 115.04, 36.38, 30.09; $^{19}$F NMR (CDCl$_3$) δ −154.16 |
| F11 | 115.0-117.8 | 358 ([M + H]$^+$) | 7.64 (t, J = 6.9 Hz, 1H), 7.61 (d, J = 3.1 Hz, 1H), 7.17 (dd, J = 9.1, 3.2 Hz, 1H), 6.94 (dd, J = 9.1, 4.4 Hz, 1H), 3.92-3.86 (m, 3H), 3.85-3.81 (m, 3H), 3.47 (d, J = 5.8 Hz, 3H), 3.18 (s, 3H) | $^{19}$F NMR (CDCl$_3$) δ −154.19; $^{13}$C NMR (CDCl$_3$) δ 153.17, 150.89, 147.05, 141.96, 139.34, 125.18, 123.36, 121.77, 116.93, 113.83, 56.92, 56.09, 36.38, 29.98 |
| F12 | 111.4-112.0 | 328 ([M + H]$^+$) | 7.64 (d, J = 9.2 Hz, 1H), 7.62-7.58 (m, 1H), 7.56-7.52 (m, 1H), 7.47 (t, J = 8.1 Hz, 1H), 7.22 (dd, J = 2.6, 0.9 Hz, 1H), 3.89 (s, 3H), 3.45 (d, J = 5.8 Hz, 3H), 3.18 (s, 3H) | $^{13}$C NMR (CDCl$_3$) δ 159.69, 146.85, 142.52, 141.64, 140.07, 137.97, 130.08, 121.24, 115.25, 113.76, 55.83, 36.37, 30.08; $^{19}$F NMR (CDCl$_3$) δ −154.50 |
| F13 | 138.9-140.3 | 346 ([M + H]$^+$) | 7.88 (ddd, J = 8.8, 2.2, 1.4 Hz, 1H), 7.73 (dd, J = 10.2, 2.3 Hz, 1H), 7.62 (d, J = 9.2 Hz, 1H), 7.13-7.04 (m, 1H), 3.98 (d, J = 4.2 Hz, 3H), 3.45 (d, J = 5.8 Hz, 3H), 3.18 (s, 3H) | $^{13}$C NMR (CDCl$_3$) δ 153.36, 152.50, 149.99, 146.90, 142.48, 140.04, 127.46, 117.22, 115.15, 112.58, 56.57, 36.37, 30.06; $^{19}$F NMR (CDCl$_3$) δ −131.07, −154.43 |
| F14 | 137.3-138.9 | 316 ([M + H]$^+$) | 7.86 (d, J = 8.0 Hz, 1H), 7.80-7.72 (m, 1H), 7.62 (d, J = 9.0 Hz, 1H), 7.60-7.53 (m, 1H), 7.40 (td, J = 8.2, 2.2 Hz, 1H), 3.46 (d, J = 5.8 Hz, 3H), 3.18 (s, 3H) | $^{13}$C NMR (101 MHz, CDCl$_3$) δ 163.25, 160.74, 146.78, 142.66, 141.37, 140.21, 138.73, 130.87, 125.08, 122.24, 116.76, 114.94, 36.40, 30.10; $^{19}$F NMR (CDCl$_3$) δ −108.66, −153.91 |
| F15 | 175.7-177.6 | 340 ([M + H]$^+$) | 7.68 (d, J = 9.2 Hz, 1H), 6.99 (s, 2H), 3.46 (d, J = 5.9 Hz, 3H), 3.17 (s, 3H), 2.62 (s, 6H), 2.31 (s, 3H) | $^{13}$C NMR (CDCl$_3$) δ 147.47, 144.64, 141.84, 141.80, 141.56, 140.88, 139.40, 132.27, 131.68, 115.43, 115.03, 36.36, 29.99, 22.75, 21.17; $^{19}$F NMR (CDCl$_3$) δ −155.15 |

TABLE 2-continued

Analytical Data for Compounds in Table 1

| No. | Mp (° C.) | ESIMS m/z | $^1$H NMR (δ)$^a$ | $^{13}$C NMR or $^{19}$F NMR (δ) |
|---|---|---|---|---|
| F16 | 123.7-125.8 | 312 ([M + H]$^+$) | 7.90-7.79 (m, 2H), 7.66 (d, J = 9.2 Hz, 1H), 7.47 (dt, J = 15.1, 7.7 Hz, 2H), 3.45 (d, J = 5.8 Hz, 3H), 3.17 (s, 3H), 2.46 (s, 3H) | $^{13}$C NMR (CDCl$_3$) δ 146.89, 142.49, 141.70, 140.04, 139.46, 136.80, 135.61, 129.21, 126.39, 115.29, 36.36, 30.06, 21.37. $^{19}$F NMR (CDCl$_3$) δ −154.67 |
| F17 | 121.1-122.6 | 304 ([M + H]$^+$) | 8.36 (dd, J = 3.1, 1.3 Hz, 1H), 7.61 (d, J = 9.2 Hz, 1H), 7.55 (dd, J = 5.2, 1.3 Hz, 1H), 7.44 (dd, J = 5.2, 3.2 Hz, 1H), 3.45 (d, J = 5.8 Hz, 3H), 3.21 (s, 3H) | $^{13}$C NMR (CDCl$_3$) δ 146.95, 142.47, 141.62, 140.02, 135.89, 127.48, 115.14, 114.73, 36.37, 30.08; $^{19}$F NMR (CDCl$_3$) δ −154.45 |
| F18 | 147.0-149.0 | 316 ([M + H]$^+$) | 8.09 (s, 1H), 7.63 (d, J = 9.2 Hz, 1H), 3.88 (s, 3H), 3.45 (d, J = 5.8 Hz, 3H), 3.21 (s, 3H), 2.40 (s, 3H) | $^{13}$C NMR (CDCl$_3$) δ 149.13, 147.05, 142.18, 139.74, 137.54, 115.41, 114.89, 39.57, 36.35, 29.98, 12.73; $^{19}$F NMR (CDCl$_3$) δ −155.09 |
| F19 | 130.1-131.1 | 317 ([M + H]$^+$) | 7.59 (d, J = 9.0 Hz, 1H), 3.47 (d, J = 5.8 Hz, 3H), 3.21 (s, 3H), 2.77 (s, 3H), 2.40 (s, 3H) | $^{13}$C NMR (CDCl$_3$) δ 178.15, 157.54, 147.06, 142.41, 141.15, 139.95, 114.64, 114.22, 113.44, 36.42, 30.06, 13.43, 10.99; $^{19}$F NMR (CDCl$_3$) δ −153.89 |
| F20 | 135.0-136.9 | 366 ([M + H]$^+$) | 7.92 (d, J = 1.9 Hz, 2H), 7.66 (t, J = 1.8 Hz, 1H), 7.58 (d, J = 8.9 Hz, 1H), 3.47 (d, J = 5.7 Hz, 3H), 3.19 (s, 3H) | $^{13}$C NMR (CDCl$_3$) δ 146.69, 142.80, 141.13, 140.89, 139.57, 135.98, 134.74, 127.51, 114.66, 36.43, 30.17; $^{19}$F NMR (CDCl$_3$) δ −153.26 |
| F21 | 109.0-112.0 | 350 ([M + H]$^+$) | 8.37 (dd, J = 9.0, 5.7 Hz, 1H), 7.66 (d, J = 9.0 Hz, 1H), 7.32-7.18 (m, 3H), 3.48 (d, J = 5.8 Hz, 3H), 3.17 (s, 3H) | $^{13}$C NMR (CDCl$_3$) δ 166.97, 164.37, 146.78, 142.21, 141.30, 139.76, 135.40, 131.26, 119.54, 115.78, 36.43, 30.03; $^{19}$F NMR (CDCl$_3$) δ −99.64, −154.17 |
| F22 | — | — | 8.05 (s, 1H), 7.66 (d, J = 9.1 Hz, 1H), 7.28 (d, J = 15.3 Hz, 1H), 3.47 (d, J = 5.8 Hz, 3H), 3.17 (s, 3H), 2.45 (d, J = 17.2 Hz, 2H) | $^{13}$C NMR (CDCl$_3$) δ 146.93, 142.28, 141.44, 139.83, 136.48, 134.97, 134.27, 133.72, 132.82, 115.08, 114.67, 36.40, 30.05, 19.87; $^{19}$F NMR (CDCl$_3$) δ −154.09 |
| F23 | — | 333 ([M + H]$^+$) | 7.61 (d, J = 9.1 Hz, 1H), 3.47 (d, J = 5.8 Hz, 3H), 3.22 (s, 3H), 2.69 (d, J = 17.5 Hz, 6H) | $^{13}$C NMR (CDCl$_3$) δ 172.37, 160.92, 139.92, 125.88, 115.07, 114.65, 36.41, 30.12, 29.71, 19.70, 17.16; $^{19}$F NMR (CDCl$_3$) δ −154.08 |
| F24 | 190-193 | 434 ([M + H]$^+$) | 8.13-7.94 (m, 3H), 7.50-7.35 (m, 2H), 7.34-7.13 (m, 4H), 7.13-6.99 (m, 2H), 3.92 (s, 3H), 3.35 (s, 3H) | $^{19}$F NMR (376 MHz, CDCl3) δ −155.78, −155.79 |
| F25 | — | 454.5 ([M + H]$^+$) | 8.29 (d, J = 5.4 Hz, 1H), 8.04 (d, J = 8.4 Hz, 2H), 7.39 (d, J = 8.3 Hz, 2H), 5.71 (s, 2H), 3.03-2.88 (m, 1H), 2.62-2.49 (m, 1H), 2.47 (s, 3H), 1.21 (d, J = 6.7 Hz, 6H), 1.13 (d, J = 7.0 Hz, 6H) | $^{13}$C NMR (CDCl$_3$) δ 178.45, 176.44, 160.96, 160.82, 149.46, 147.31, 141.06, 138.55, 131.61, 130.46, 129.81, 127.60, 127.23, 69.50, 33.72, 33.34, 21.88, 19.39, 18.67 |

TABLE 2-continued

Analytical Data for Compounds in Table 1

| No. | Mp (° C.) | ESIMS m/z | $^1$H NMR (δ)$^a$ | $^{13}$C NMR or $^{19}$F NMR (δ) |
|---|---|---|---|---|
| F26 | — | 356.4 ([M + H]$^+$) | 8.04-7.94 (m, 2H), 7.90 (d, J = 6.7 Hz, 1H), 7.08-6.99 (m, 2H), 3.91 (s, 3H), 3.23 (s, 3H), 2.23 (d, J = 1.0 Hz, 3H) | $^{19}$F NMR (376 MHz, CDCl$_3$) δ −153.50; $^{13}$C NMR (101 MHz, CDCl$_3$) δ 181.27, 165.11, 146.27, 138.98, 136.59, 132.12, 126.77, 118.04, 117.65, 114.49, 104.07, 55.92, 30.26, 25.92 |
| F27 | 124-125 | 372 ([M + H]$^+$) | 8.07-7.97 (m, 2H), 7.91 (d, J = 6.8 Hz, 1H), 7.14-6.95 (m, 2H), 3.91 (s, 3H), 3.80 (s, 3H), 3.27 (s, 3H) | $^{13}$C NMR (101 MHz, CDCl3) δ 165.17, 160.30, 146.05, 144.60, 139.08, 132.17, 126.63, 118.32, 117.93, 114.51, 77.32, 77.21, 77.01, 76.69, 55.92, 53.62, 30.42; $^{19}$F NMR (376 MHz, CDCl3) δ −156.51, −156.51 |
| F28 | 102.2-104.0 | 262 ([M + H]$^+$) | $^1$H NMR (DMSO-d$_6$) δ 7.63 (d, J = 9.6 Hz, 1H), 3.47-3.39 (m, 1H), 3.37 (d, J = 5.9 Hz, 3H), 3.18 (s, 3H), 1.32-1.19 (m, 4H) | $^{13}$C NMR (DMSO-d$_6$) δ 147.10, 141.64, 139.23, 116.09, 115.68, 35.70, 31.60, 29.77, 6.68 |
| F29 | 134.6-136.2 | 340 ([M + H]$^+$) | 7.92 (dd, J = 11.9, 7.5 Hz, 3H), 7.40 (d, J = 8.1 Hz, 2H), 3.22 (s, 3H), 2.48 (s, 3H), 2.23 (d, J = 0.9 Hz, 3H) | $^{13}$C NMR (CDCl$_3$) δ 181.20, 146.95, 132.91, 129.92, 129.54, 117.93, 117.54, 30.28, 25.93, 25.89, 21.87 |
| F30 | Dec 174 | 326 ([M + H]$^+$) | $^1$H NMR (DMSO-d$_6$) δ 8.30 (d, J = 7.3 Hz, 1H), 8.08 (d, J = 7.4 Hz, 2H), 7.85 (t, J = 7.5 Hz, 1H), 7.71 (t, J = 7.9 Hz, 2H), 3.07 (s, 3H), 2.13 (s, 3H) | — |
| F31 | Dec 156 | 326 ([M + H]$^+$) | $^1$H NMR (DMSO-d$_6$) δ 8.26 (d, J = 7.4 Hz, 1H), 8.00 (d, J = 9.1 Hz, 2H), 7.20 (d, J = 9.1 Hz, 2H), 3.88 (s, 3H), 3.06 (s, 3H), 2.11 (s, 3H) | — |
| F32 | Dec 158 | 354 ([M + H]$^+$) | $^1$H NMR (DMSO-d$_6$) δ 8.27 (d, J = 7.3 Hz, 1H), 7.97 (d, J = 8.4 Hz, 2H), 7.53 (d, J = 8.4 Hz, 2H), 3.05 (s, 3H), 2.72 (t, J = 11.4 Hz, 2H), 2.10 (s, 3H), 1.20 (t, J = 7.6 Hz, 3H) | — |
| F33 | Dec 165 | 368 ([M + H]$^+$) | $^1$H NMR (DMSO-d$_6$) δ 8.28 (d, J = 7.3 Hz, 1H), 7.99 (d, J = 8.5 Hz, 2H), 7.58 (d, J = 8.5 Hz, 2H), 3.09-2.82 (m, 4H), 2.12 (s, 3H), 1.23 (d, J = 6.9 Hz, 6H) | — |
| F34 | Dec 164 | 340 ([M + H]$^+$) | $^1$H NMR (DMSO-d$_6$) δ 8.28 (d, J = 7.3 Hz, 1H), 7.94-7.81 (m, 2H), 7.70-7.54 (m, 2H), 3.07 (s, 3H), 2.43 (s, 3H), 2.13 (s, 3H) | — |
| F35 | Dec 173 | 388 ([M + H]$^+$) | $^1$H NMR (DMSO-d$_6$) δ 8.33 (d, J = 7.2 Hz, 1H), 8.03 (s, 1H), 7.61 (s, 1H), 3.04 (s, 3H), 2.46 (s, 3H), 2.39 (s, 3H), 2.12 (s, 3H) | — |
| F36 | Dec 154 | 401 ([M + H]$^+$) | $^1$H NMR (DMSO-d$_6$) δ 8.24 (d, J = 7.2 Hz, 1H), 7.65 (s, 1H), 3.12 (s, 3H), 2.15 (s, 3H) | — |
| F37 | 180.8-182.2 | 492 ([M + H]$^+$) | 8.03-7.88 (m, 5H), 7.77-7.65 (m, 3H), 7.52 (dd, J = 14.1, 6.2 Hz, 3H), 7.43-7.30 (m, 4H), 2.47 (s, 3H) | $^{13}$C NMR (CDCl$_3$) δ 174.91, 170.80, 166.51, 147.41, 146.77, 144.69, 135.72, 133.99, 133.25, 132.54, 130.76, 130.54, 130.43, 130.12, 129.99, 129.86, 129.72, 129.69, 129.47, 125.97, 120.01, 119.63, 50.14 21.88, 21.8 |

TABLE 2-continued

Analytical Data for Compounds in Table 1

| No. | Mp (° C.) | ESIMS m/z | ¹H NMR (δ)$^a$ | ¹³C NMR or ¹⁹F NMR (δ) |
|---|---|---|---|---|
| F38 | 170-171 | 426 ([M + Na]⁺) | 8.09 (d, J = 8.6 Hz, 2H), 8.01 (d, J = 6.6 Hz, 2H), 7.77 (t, J = 7.5 Hz, 1H), 7.64 (t, J = 7.9 Hz, 2H), 7.41 (t, J = 7.9 Hz, 2H), 7.19 (d, J = 8.1 Hz, 2H), 3.35 (s, 3H) | — |
| F39 | 200-202 | 440 ([M + Na]⁺) | 7.99 (dd, J = 18.1, 7.5 Hz, 2H), 7.41 (t, J = 7.8 Hz, 3H), 7.29-7.16 (m, 5H), 3.35 (s, 3H), 2.49 (s, 3H) | — |
| F40 | 188-190 | 454 ([M + Na]⁺) | 8.05-7.96 (m, 3H), 7.47-7.38 (m, 5H), 7.19 (d, J = 8.1 Hz, 2H), 3.35 (s, 3H), 2.78 (q, J = 7.6 Hz, 2H), 1.30 (t, J = 7.6 Hz, 3H) | — |
| F41 | 180-181 | 468 ([M + Na]⁺) | 8.01 (dd, J = 7.6, 4.6 Hz, 3H), 7.50-7.37 (m, 3H), 7.27-7.16 (m, 4H), 3.36 (s, 3H), 3.04 (dt, J = 13.6, 6.9 Hz, 1H), 1.30 (d, J = 6.9 Hz, 6H) | — |
| F42 | 187-188 | 440 ([M + Na]⁺) | 8.01 (d, J = 6.6 Hz, 1H), 7.89 (d, J = 7.7 Hz, 1H), 7.84 (s, 1H), 7.52 (dt, J = 15.4, 7.7 Hz, 2H), 7.40 (t, J = 7.9 Hz, 2H), 7.30-7.15 (m, 3H), 3.34 (s, 3H), 2.49 (s, 3H) | — |
| F43 | 209-211 | 488 ([M + Na]⁺) | ¹H NMR (DMSO-d₆) δ 8.52 (d, J = 7.3 Hz, 1H), 8.06 (s, 1H), 7.63 (s, 1H), 7.45 (t, J = 7.9 Hz, 2H), 7.28 (t, J = 7.4 Hz, 1H), 7.16 (d, J = 8.0 Hz, 2H), 3.15 (s, 3H), 2.41 (s, 6H) | — |
| F44 | 158-159 | 499 ([M + Na]⁺) | 7.96 (d, J = 6.5 Hz, 1H), 7.48-7.37 (m, 3H), 7.31-7.23 (m, 2H), 7.20 (d, J = 7.6 Hz, 1H), 3.41 (s, 3H) | — |
| F45 | 185-186 | 364 ([M + Na]⁺) | 8.04 (d, J = 8.2 Hz, 2H), 7.89 (d, J = 6.7 Hz, 1H), 7.73 (t, J = 7.5 Hz, 1H), 7.59 (t, J = 7.9 Hz, 2H), 3.78 (s, 3H), 3.24 (s, 3H) | — |
| F46 | 145-146 | 378 ([M + Na]⁺) | 7.92 (t, J = 7.8 Hz, 3H), 7.40 (d, J = 8.1 Hz, 2H), 3.80 (s, 3H), 3.26 (s, 3H), 2.48 (s, 3H) | — |
| F47 | 125-126 | 392 ([M + Na]⁺) | 7.94 (dd, J = 17.7, 7.6 Hz, 3H), 7.42 (d, J = 8.3 Hz, 2H), 3.80 (s, 3H), 3.27 (s, 3H), 2.83-2.66 (m, 2H), 1.28 (t, J = 7.6 Hz, 3H) | — |
| F48 | 116-117 | 406 ([M + Na]⁺) | 7.94 (dd, J = 21.7, 7.6 Hz, 3H), 7.44 (d, J = 8.5 Hz, 2H), 3.80 (s, 3H), 3.27 (s, 3H), 3.02 (dt, J = 13.8, 6.9 Hz, 1H), 1.29 (d, J = 6.9 Hz, 6H) | — |
| F49 | 200-201 | 378 ([M + Na]⁺) | 7.97-7.77 (m, 3H), 7.51 (dt, J = 15.3, 7.7 Hz, 2H), 3.80 (s, 3H), 3.27 (s, 3H), 2.48 (s, 3H) | — |
| F50 | 178-179 | 426 ([M + Na]⁺) | 8.04 (s, 1H), 7.92 (d, J = 6.6 Hz, 1H), 7.34 (s, 1H), 3.82 (s, 3H), 3.27 (s, 3H), 2.46 (d, J = 10.6 Hz, 6H) | — |
| F51 | 148-149 | 437 ([M + Na]+) | 7.96 (d, J = 6.5 Hz, 1H), 7.20 (d, J = 7.6 Hz, 1H), 3.80 (s, 3H), 3.27 (s, 3H) | — |
| F52 | 189-192 | 414 ([M + Na]⁺) | 8.06 (d, J = 7.4 Hz, 2H), 7.71 (dd, J = 16.7, 8.3 Hz, 2H), 7.58 (t, J = 7.8 Hz, 2H), 7.46 (t, J = 7.9 Hz, | — |

TABLE 2-continued

Analytical Data for Compounds in Table 1

| No. | Mp (° C.) | ESIMS m/z | $^1$H NMR (δ)$^a$ | $^{13}$C NMR or $^{19}$F NMR (δ) |
|---|---|---|---|---|
| | | | 1H), 7.30-7.16 (m, 1H), 7.11 (t, J = 7.5 Hz, 1H), 7.07-6.97 (m, 1H), 4.97 (s, 2H), 3.26 (s, 3H) | |
| F53 | 188-191 | 444 ([M + Na]$^+$) | 8.01 (d, J = 9.0 Hz, 2H), 7.73 (d, J = 9.1 Hz, 1H), 7.47 (t, J = 7.8 Hz, 1H), 7.28-7.17 (m, 1H), 7.12 (t, J = 7.5 Hz, 1H), 7.07-6.97 (m, 3H), 4.98 (s, 2H), 3.90 (s, 3H), 3.28 (s, 3H) | — |
| F54 | 184-187 | 428 ([M + Na]$^+$) | 7.95 (d, J = 8.4 Hz, 2H), 7.74 (d, J = 9.0 Hz, 1H), 7.47 (t, J = 7.6 Hz, 1H), 7.37 (d, J = 8.1 Hz, 2H), 7.24-7.19 (m, 1H), 7.12 (t, J = 7.5 Hz, 1H), 7.08-6.95 (m, 1H), 4.98 (s, 2H), 3.27 (s, 3H), 2.46 (s, 3H) | — |
| F55 | 140-141 | 442 ([M + Na]$^+$) | 7.97 (d, J = 8.4 Hz, 2H), 7.74 (d, J = 9.0 Hz, 1H), 7.47 (t, J = 7.4 Hz, 1H), 7.40 (d, J = 8.4 Hz, 2H), 7.25-7.17 (m, 1H), 7.12 (t, J = 7.4 Hz, 1H), 7.08-6.96 (m, 1H), 4.98 (s, 2H), 3.27 (s, 3H), 2.75 (q, J = 7.6 Hz, 2H), 1.27 (t, J = 7.6 Hz, 3H) | — |
| F56 | 140-143 | 456 ([M + Na]$^+$) | 7.97 (d, J = 8.5 Hz, 2H), 7.73 (d, J = 9.1 Hz, 1H), 7.46 (t, J = 7.6 Hz, 1H), 7.41 (d, J = 8.4 Hz, 2H), 7.25-7.15 (m, 1H), 7.11 (t, J = 7.4 Hz, 1H), 7.06-6.96 (m, 1H), 4.97 (s, 2H), 3.27 (s, 3H), 3.10-2.95 (m, 1H), 1.27 (d, J = 6.9 Hz, 6H) | — |
| F57 | 177-180 | 428 ([M + Na]$^+$) | 7.94-7.82 (m, 2H), 7.77 (d, J = 9.0 Hz, 1H), 7.56-7.45 (m, 3H), 7.29-7.19 (m, 1H), 7.15 (t, J − 7.4 Hz, 1H), 7.11-6.95 (m, 1H), 5.01 (s, 2H), 3.30 (s, 3H), 2.49 (s, 3H) | — |
| F58 | 208-210 | 476 ([M + Na]$^+$) | 8.03 (s, 1H), 7.71 (d, J = 8.9 Hz, 1H), 7.46 (t, J = 7.6 Hz, 1H), 7.29 (s, 1H), 7.23-7.18 (m, 1H), 7.11 (t, J = 7.2 Hz, 1H), 7.06-6.96 (m, 1H), 4.98 (s, 2H), 3.25 (s, 3H), 2.47 (s, 3H), 2.42 (s, 3H) | — |
| F59 | 108-111 | — | 7.69 (d, J = 8.8 Hz, 1H), 7.49 (t, J = 7.5 Hz, 1H), 7.37 (s, 1H), 7.25-7.20 (m, 1H), 7.14 (t, J = 7.4 Hz, 1H), 7.09-6.98 (m, 1H), 5.01 (s, 2H), 3.33 (s, 3H) | — |
| F61 | — | 304.1 ([M + H]$^+$) | 8.07-8.04 (d, J = 8.8 Hz, 2H), 7.73-7.64 (m, 3H), 7.60-7.54 (m, 2H) | $^{19}$F NMR (376 MHz, CDCl$_3$) δ −154.6 |
| F62 | — | 333.8 ([M + H]$^+$) | 7.99 (d, J = 9.2 Hz, 2H), 7.72 (m, 1H), 7.65 (d, J = 9.2 Hz, 2H), 7.05-6.97 (m, 2H), 3.89 (s, 3H) | $^{19}$F NMR (376 MHz, CDCl$_3$) δ −155.2 |
| F63 | — | 318.0 ([M + H]$^+$) | 7.93 (d, J = 8.8 Hz, 2H), 7.65 (d, J = 8.8 Hz, 2H), 7.38-7.35 (m, 1H), 2.46 (s, 3H) | $^{19}$F NMR (376 MHz, CDCl$_3$) δ −154.9 |

$^a$All $^1$H NMR data measured in CDCl$_3$ at 400 MHz unless otherwise noted.

The following table presents the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

In each case of Table I the rating scale is as follows:

| % Disease Control | Rating |
|---|---|
| 76-100 | A |
| 51-75 | B |
| 26-50 | C |
| 0-25 | D |
| Not Tested | E |

TABLE 3

One-Day Protectant (1 DP) and Three-Day Curative (3 DC) Activity of Compounds on SEPTTR at 100 ppm

| Cmpd | SEPTTR 100 PPM 1 DP | SEPTTR 100 PPM 3 DC |
|---|---|---|
| F1 | A | B |
| F2 | A | B |
| F3 | A | B |
| F4 | A | A |
| F5 | A | A |
| F6 | A | A |
| F7 | C | B |
| F8 | A | A |
| F9 | A | A |
| F10 | A | B |
| F11 | A | A |
| F12 | A | A |
| F13 | A | A |
| F14 | A | B |
| F15 | C | C |
| F16 | C | D |
| F17 | A | A |
| F18 | C | A |
| F19 | D | B |
| F20 | C | D |
| F21 | E | E |
| F22 | A | A |
| F23 | C | A |
| F24 | D | D |
| F25 | D | A |
| F26 | A | A |
| F27 | D | D |
| F28 | D | B |
| F29 | A | A |
| F30 | A | A |
| F31 | A | A |
| F32 | A | A |
| F33 | A | C |
| F34 | A | D |
| F35 | A | C |
| F36 | A | B |
| F37 | D | D |
| F38 | A | A |
| F39 | C | C |
| F40 | D | D |
| F41 | D | D |
| F42 | A | D |
| F43 | D | D |
| F44 | A | A |
| F45 | D | D |
| F46 | D | D |
| F47 | D | D |
| F48 | D | D |
| F49 | D | D |
| F50 | D | D |

TABLE 3-continued

One-Day Protectant (1 DP) and Three-Day Curative (3 DC) Activity of Compounds on SEPTTR at 100 ppm

| Cmpd | SEPTTR 100 PPM 1 DP | SEPTTR 100 PPM 3 DC |
|---|---|---|
| F51 | D | D |
| F52 | D | D |
| F53 | D | D |
| F54 | D | D |
| F55 | D | D |
| F56 | D | D |
| F57 | D | D |
| F58 | D | D |
| F59 | D | D |
| F61 | D | D |
| F62 | D | D |
| F63 | D | D |

What is claimed is:

1. A method for the control or prevention of fungal attack on a plant comprising applying a fungicidal composition comprising a fungicidally effective amount of at least one compound of Formula I and a phytologically acceptable carrier material to at least one of the fungus, the plant, an area adjacent to the plant and the seed adapted to produce the plant,

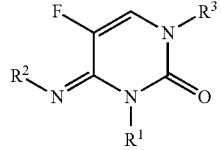

Formula I wherein $R^1$ is:
$C_1$-$C_6$ alkyl optionally substituted with 1-3 $R^4$;
—C(=O) $R^5$;
—C(=O)O$R^5$;
—CH$_2$OC(=O)$R^5$; or
—(CHR$^8$)$_n$$R^7$;

$R^2$ is:
$C_1$-$C_6$ alkyl optionally substituted with 1-3 $R^6$;
—C(=O)$R^7$;
—C(=O)O$R^7$; or
—(CHR$^8$)$_n$$R^7$;
wherein n is an integer from 1-3;

$R^3$ is —S(O)$_2$$R^9$;

$R^4$ is independently $C_1$-$C_6$ alkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, deuterium, or $C_3$-$C_6$ trialkylsilyl;

$R^5$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^{10}$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^{10}$, biphenyl or naphthyl optionally substituted with 1-3 $R^{10}$;

$R^6$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, deuterium, or $C_3$-$C_6$ trialkylsilyl;

$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^{10}$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^{10}$, biphenyl or naphthyl optionally substituted with 1-3 $R^{10}$;

$R^8$ is H, $C_1$-$C_6$ alkyl, or $C_1$-$C_6$ haloalkyl;

$R^9$ is $C_1$-$C_6$ alkyl, $C_1$-$C_6$ haloalkyl, amino, $C_1$-$C_6$ alkylamino, $C_2$-$C_6$ dialkylamino, a phenyl or benzyl wherein each of the phenyl or the benzyl may be optionally substituted with 1-3 $R^{10}$, or a 5- or 6-membered saturated or unsaturated ring containing 1-3 heteroatoms wherein each ring may be optionally substituted with 1-3 $R^{10}$, or with a 5-6 fused ring system, or with a 6-6 fused ring system each containing 1-3 heteroatoms wherein each ring may be optionally substituted with 1-3 $R^{10}$, biphenyl or naphthyl optionally substituted with 1-3 $R^{10}$; and $R^{10}$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_6$ alkylamino, $C_2$-$C_6$ alkoxycarbonyl, $C_2$-$C_6$ alkylcarbonyl, $C_2$-$C_6$ alkylaminocarbonyl, $C_2$-$C_6$ dialkylamino, hydroxy, cyano, or nitro, or an optical isomer, a salt, or a hydrate thereof.

2. The method of claim 1, wherein the compound of Formula I is in the form of a salt.

3. The method of claim 2, wherein the salt is a hydrochloride, hydroiodide or hydrobromide.

4. The method of claim 1, wherein the fungicidal composition further comprises an adjuvant surfactant.

5. The method of claim 1, wherein the fungicidal composition further comprises an emulsifier.

6. The method of claim 1, wherein the fungicidal composition further comprises at least one additional pesticidal compound.

7. The method of claim 6, wherein the additional pesticidal compound is selected from fungicides, insecticides, herbicides, nematicides, miticides, arthropodicides, or bactericides.

8. The method of claim 1, wherein the fungicidal composition is a solution, dust, wettable powder, water dispersable granules, flowable concentrate, emulsifiable concentrate, aqueous suspension, or emulsion.

9. The method of claim 1, wherein the compound of Formula I is applied in conjunction with one or more other fungicide(s).

10. The method of claim 1, wherein the compound of Formula I is selected from:

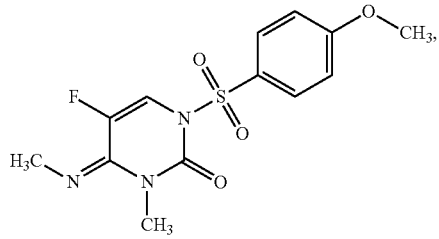

-continued

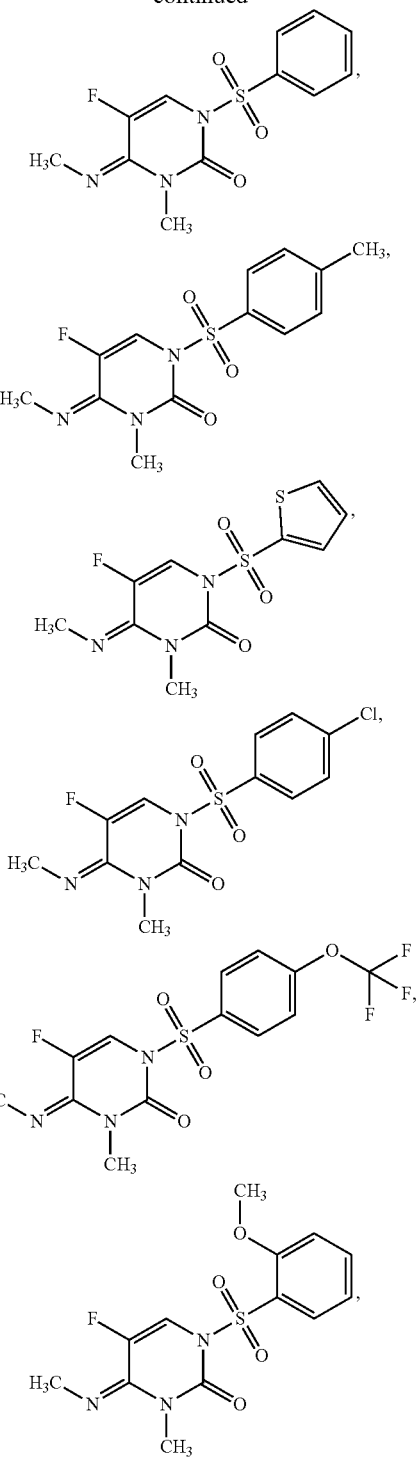

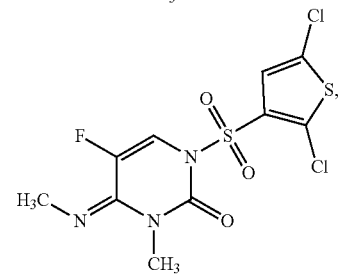

-continued
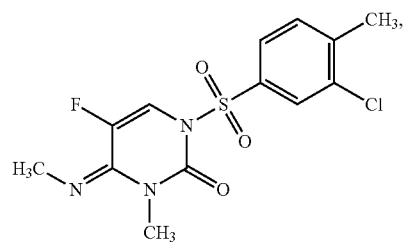
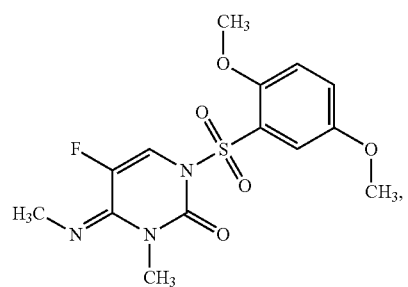
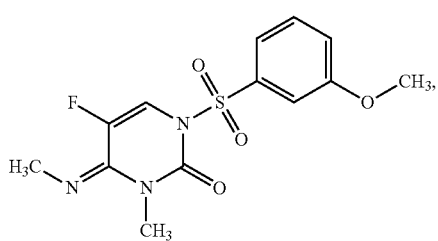
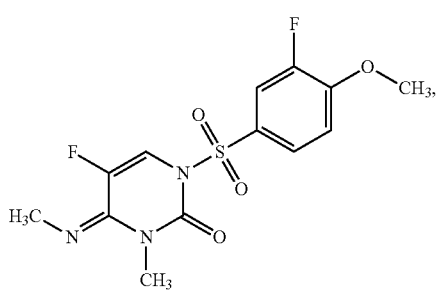
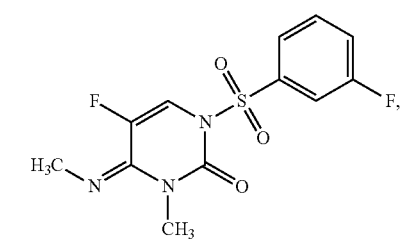
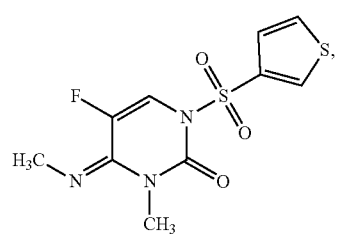
-continued
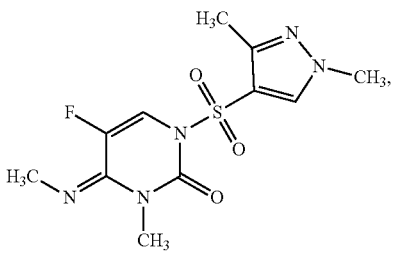
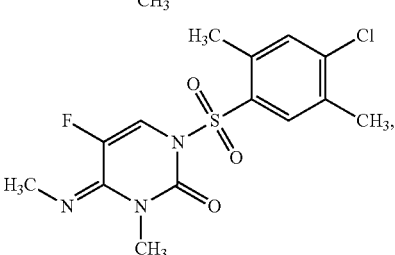
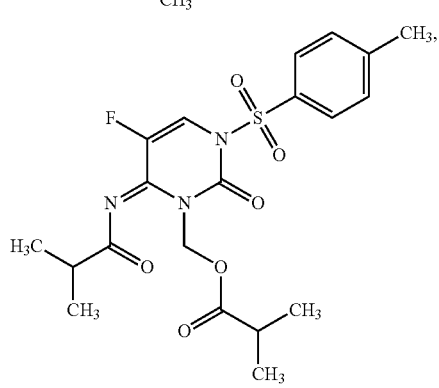
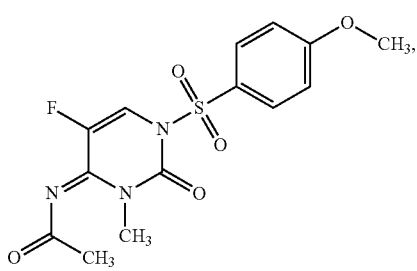
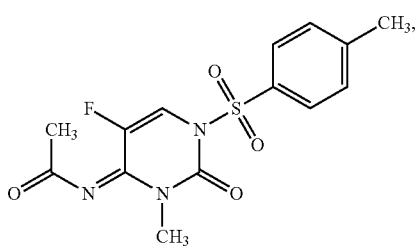
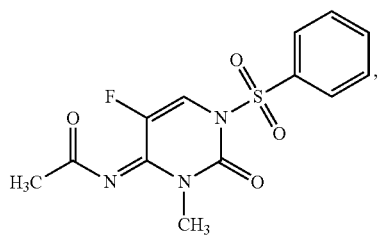

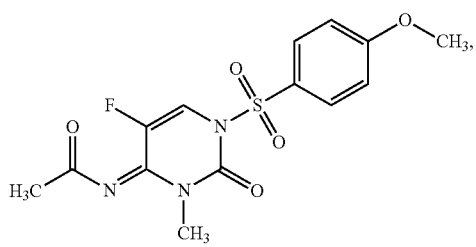
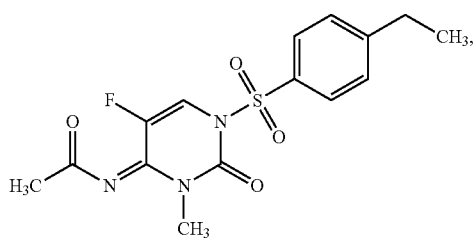
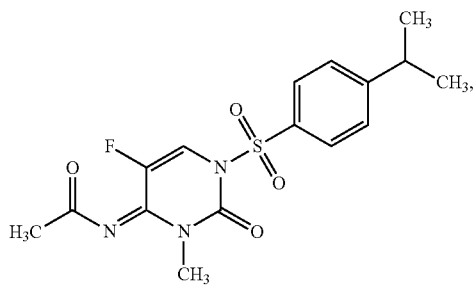
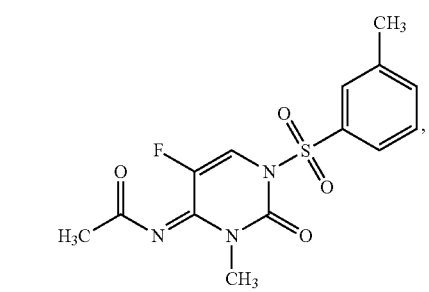
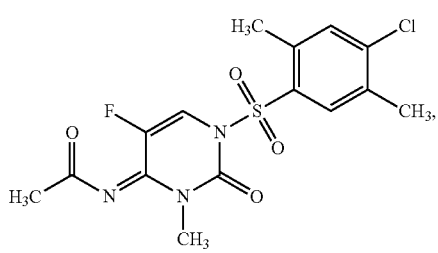
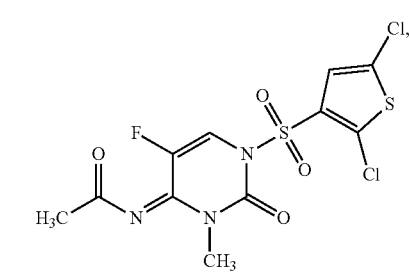
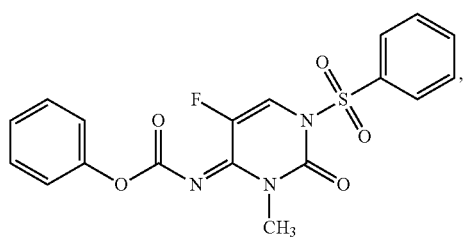
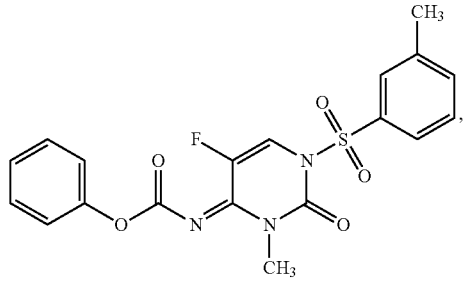
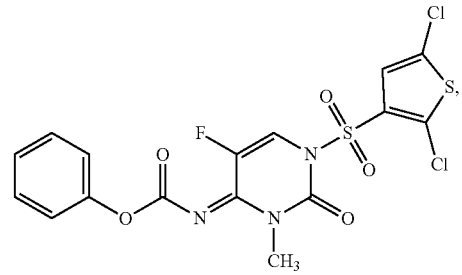
and salts thereof.
11. The method of claim 1, wherein the compound of Formula I is selected from:
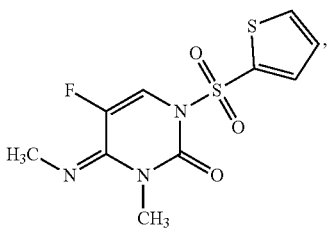
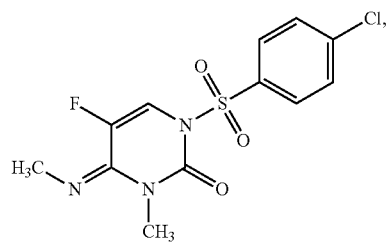
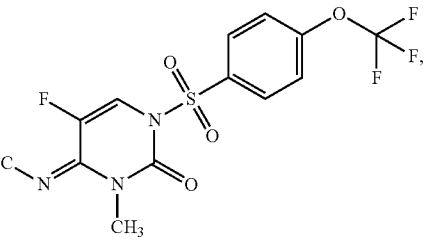

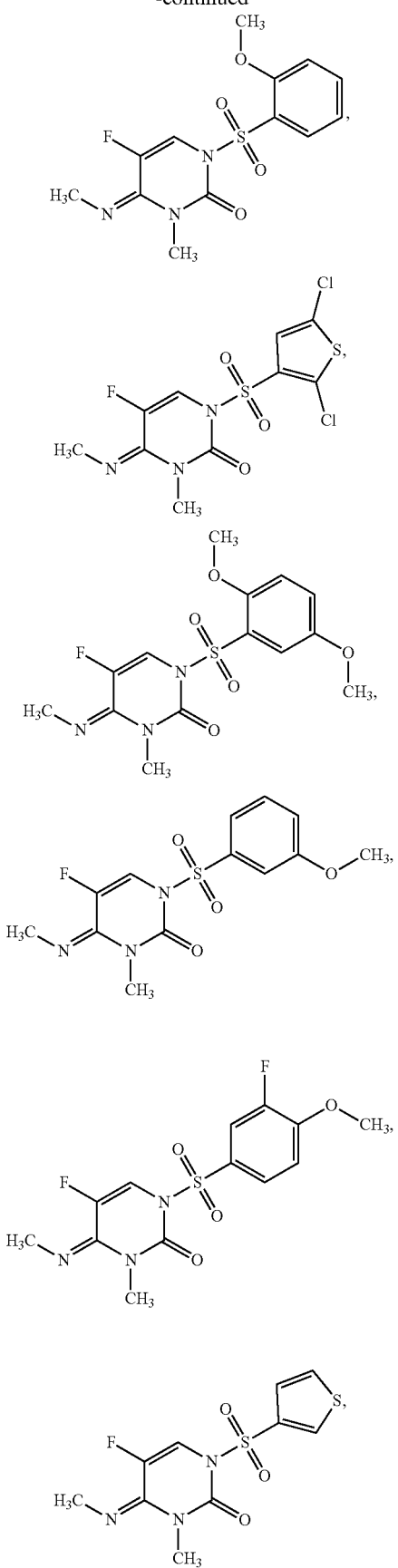
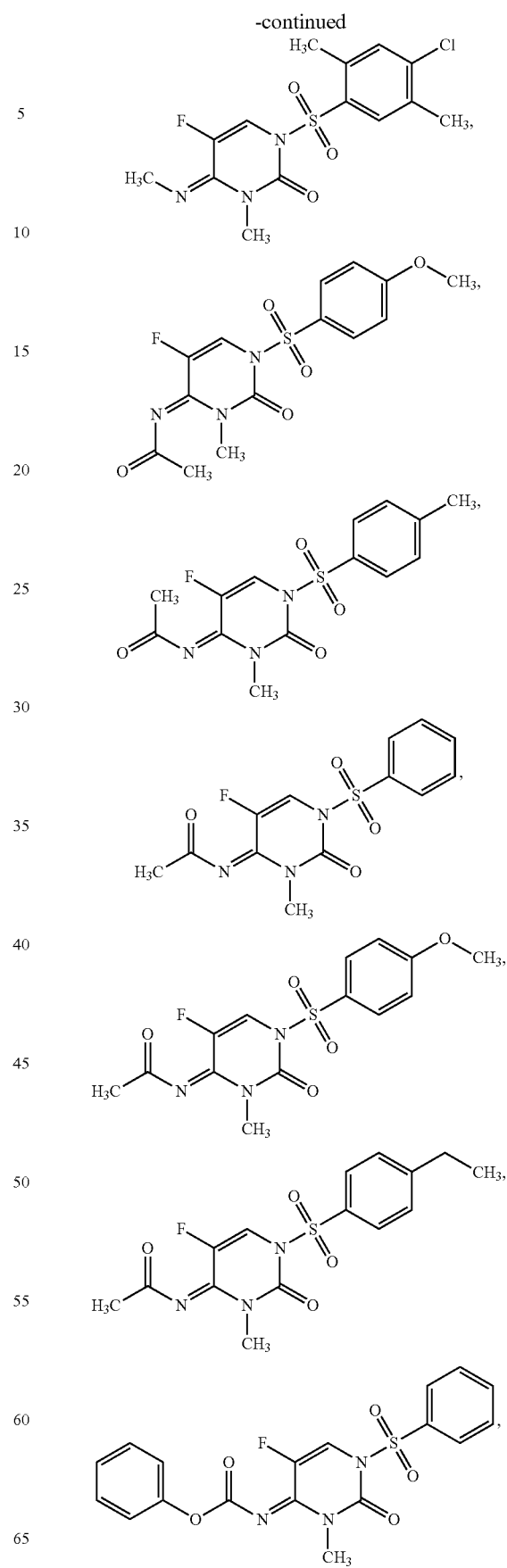

-continued

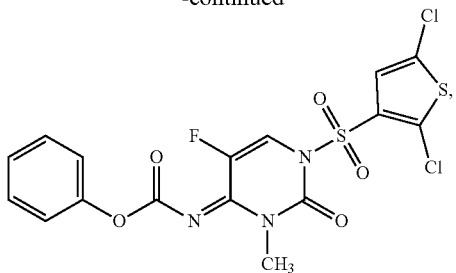

and salts thereof.

12. The method of claim 1, wherein the fungal pathogen is selected from ascomycetes, basidiomycetes, deuteromycetes and oomycetes.

13. The method of claim 1, wherein the fungal pathogen is wheat leaf blotch (*Septoria tritici*), apple scab (*Venturia inaequalis*), *Cercospora* leaf spots of sugar beets (*Cercospora beticola*), leaf spots of peanut (*Cercospora arachidicola* and *Cercosporidium personatum*) or black sigatoka of bananas (*Mycosphaerella fujiensis*).

14. The method of claim 1, wherein the fungal pathogen is wheat leaf blotch (*Septoria tritici*).

15. The method of claim 1, wherein the method is effective to improve the health of the plant.

16. The method of claim 1, wherein the method is effective to improve the yield of the plant.

17. The method of claim 1, wherein the method is effective to improve the vigor of the plant.

18. The method of claim 1, wherein the method is effective to improve the quality of the plant.

19. The method of claim 1, wherein the method is effective to improve the tolerance of the plant to abiotic stress.

20. The method of claim 1, wherein the method is effective to improve the tolerance of the plant to biotic stress.

* * * * *